US009193994B2

(12) United States Patent
Park et al.

(10) Patent No.: US 9,193,994 B2
(45) Date of Patent: Nov. 24, 2015

(54) POLYNUCLEOTIDE AND USE THEREOF

(71) Applicant: Samsung Electronics Co., Ltd., Suwon-si, Gyeonggi-do (KR)

(72) Inventors: Dong-hyun Park, Chuncheon-si (KR); Sung-woo Hong, Yongin-si (KR); Myo-yong Lee, Suwon-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 85 days.

(21) Appl. No.: 13/866,655

(22) Filed: Apr. 19, 2013

(65) Prior Publication Data

US 2013/0280713 A1 Oct. 24, 2013

(30) Foreign Application Priority Data

Apr. 20, 2012 (KR) .................. 10-2012-0041601
Nov. 13, 2012 (KR) .................. 10-2012-0128369

(51) Int. Cl.
*C12Q 1/68* (2006.01)
*C12P 19/34* (2006.01)
*C07H 21/00* (2006.01)

(52) U.S. Cl.
CPC ............ *C12Q 1/6853* (2013.01); *C12Q 1/6844* (2013.01); *C12Q 2525/161* (2013.01)

(58) Field of Classification Search
CPC .......... C12Q 1/68; C12Q 1/6806; C12P 19/34
USPC ........................ 435/6.1; 536/22.1, 23.1, 24.3
See application file for complete search history.

(56) References Cited

U.S. PATENT DOCUMENTS

| | | | |
|---|---|---|---|
| 5,942,391 A * | 8/1999 | Zhang et al. ................. | 435/6.12 |
| 6,287,825 B1 | 9/2001 | Weissman et al. | |
| 6,368,801 B1 * | 4/2002 | Faruqi .......................... | 435/6.12 |
| 6,558,928 B1 * | 5/2003 | Landegren ................... | 435/91.1 |
| 6,811,986 B2 * | 11/2004 | Bandaru et al. ............. | 435/6.12 |
| 6,830,884 B1 * | 12/2004 | Hafner et al. ............... | 435/6.12 |
| 7,365,187 B2 | 4/2008 | Hashiguchi et al. | |
| 7,575,863 B2 | 8/2009 | Chen et al. | |
| 7,700,323 B2 * | 4/2010 | Willis et al. ................. | 435/91.1 |
| 8,008,010 B1 * | 8/2011 | Kuersten et al. ............ | 435/6.11 |
| 8,192,937 B2 | 6/2012 | Jacobsen et al. | |
| 2001/0039039 A1 * | 11/2001 | Weissman et al. .......... | 435/91.1 |
| 2003/0017591 A1 * | 1/2003 | Kurn .............................. | 435/400 |
| 2004/0067511 A1 * | 4/2004 | Thomas .......................... | 435/6 |
| 2004/0171047 A1 | 9/2004 | Dahl et al. | |
| 2005/0079523 A1 * | 4/2005 | Hafner et al. .................... | 435/6 |
| 2005/0266418 A1 | 12/2005 | Chen et al. | |
| 2006/0223098 A1 | 10/2006 | Lane et al. | |
| 2007/0003940 A1 | 1/2007 | Wang | |
| 2007/0292878 A1 | 12/2007 | Raymond | |
| 2008/0131878 A1 | 6/2008 | Latham et al. | |
| 2009/0220969 A1 | 9/2009 | Chiang et al. | |
| 2009/0258353 A1 | 10/2009 | Yoon et al. | |
| 2010/0112644 A1 | 5/2010 | Kim et al. | |
| 2010/0209932 A1 | 8/2010 | Spier | |
| 2010/0291548 A1 * | 11/2010 | Sharaf et al. .................... | 435/6 |
| 2010/0317062 A1 | 12/2010 | Lao et al. | |
| 2012/0071332 A1 | 3/2012 | Busk | |
| 2012/0077191 A1 * | 3/2012 | Gunning et al. ............. | 435/6.11 |
| 2013/0085083 A1 * | 4/2013 | Kamberov et al. ............ | 506/16 |
| 2014/0038238 A1 * | 2/2014 | Zhang ........................ | 435/91.51 |
| 2014/0141418 A1 | 5/2014 | Park et al. | |

FOREIGN PATENT DOCUMENTS

| | | |
|---|---|---|
| KR | 2009-017670 A | 2/2008 |
| WO | WO 2006/108423 A2 | 10/2006 |
| WO | WO 2010/120803 A2 | 10/2010 |

OTHER PUBLICATIONS

Baner et al.Parallel gene analysis with allele-specific padlock probes and tag microarrays. Nucleic Acids Research 31 (17) :e103 (2003).*
Jonstrup et al. A microRNA detection system based on padlock probes and rolling circle amplification. RNA 12 :1747 (2006).*
Akhras et al.Connector Inversion Probe Technology: A Powerful One-Primer Multiplex DNA Amplification System for Numerous Scientific Applications. PLoS ONE 9 : e915 (2007).*
Hardenbol et al., Multiplexed genotyping with sequence-tagged molecular inversion probes. Nature Biotechnology 21(6) : 673 (2003).*
Liu et al., Pyrophosphorolysis-Activated Polymerization (PAP): Application to Allele-Specific Amplification BioTechniques 29:1072 (2000).*
Nilsson et al. Real-time monitoring of rolling-circle amplification using a modified molecular beacon design. Nucleic Acids Research 30 (14) : e66 (2002).*
Wang et al.Allele quantification using molecular inversion probes (MIP). Nucleic Acids Research 33 (21) :e183 (2005).*
Dahl et al., "Circle-to-circle amplification for precise and sensitive DNA analysis," *Proc. of the Nat'l Acad. of Sciences*, Mar. 30, 2004, 101(13), pp. 4548-4553.
European Patent Office, Extended European Search Report in European Patent Application No. 13164440.3, Jul. 10, 2013, 8 pp.
Linsen et al., "Limitations and possibilities of small RNA digital gene expression profiling", Nature Methods,6(7); 474-476( 2009).
Untergrasser et al. "Primer 3—new capabilities and interfaces", Nucleic Acids Research 40(15):e115 (2015) (printout of database page only; available online at <<http://frodo.wi.mit.edu/primer3/>>).

* cited by examiner

*Primary Examiner* — Ethan C Whisenant
(74) *Attorney, Agent, or Firm* — Leydig, Voit & Mayer, Ltd.

(57) ABSTRACT

A first polynucleotide including at least two complementary regions that are complementary to a target nucleic acid and have a reverse configuration, a second polynucleotide complementary to the first polynucleotide, and uses thereof, are provided.

10 Claims, 8 Drawing Sheets

FIG. 1A
FIG. 1B
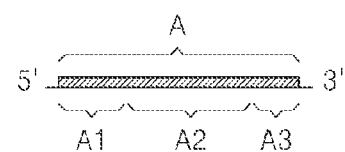
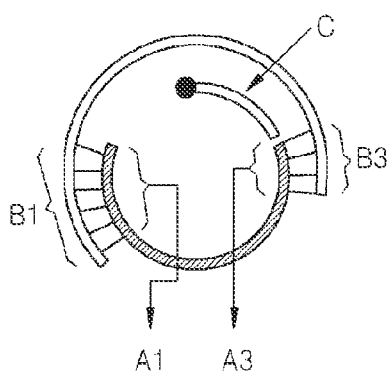
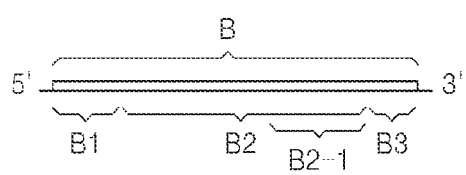
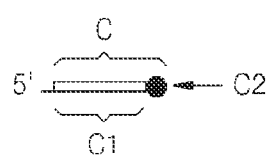
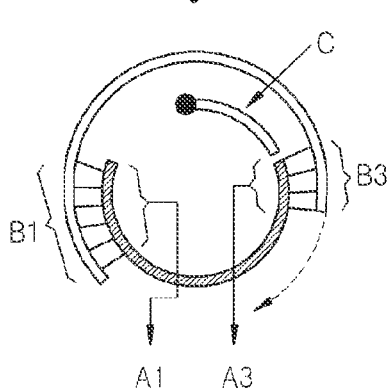
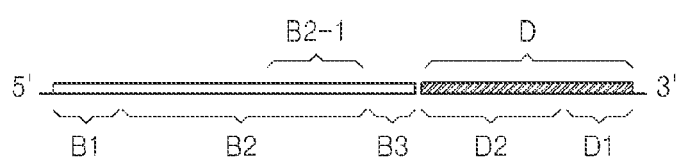

POLYNUCLEOTIDE AND USE THEREOF

CROSS-REFERENCE TO RELATED APPLICATIONS

This application claims the benefit of Korean Patent Applications No. 10-2012-0041601, filed on Apr. 20, 2012, and 10-2012-0128369, filed on Nov. 13, 2012 in the Korean Intellectual Property Office, the disclosures of which are incorporated herein in their entireties by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 39,675 Byte ASCII (Text) file named "712264_ST25.TXT," created on Apr. 18, 2013.

BACKGROUND

1. Field

The present disclosure relates to a first polynucleotide including at least two complementary regions that are complementary to a target nucleic acid and have a reverse configuration, a second polynucleotide complementary to the first polynucleotide, and uses thereof.

2. Description of the Related Art

Methods of amplifying nucleic acids include extending a nucleotide sequence from the 3'-terminal of a primer in the presence of a nucleic acid polymerase. The primer includes a sequence complementary to that of a target nucleic acid. To extend nucleotide sequences, primers and target nucleic acids need to be specifically and stably hybridized with each other. The stability of the hybridized product of nucleic acids is known to be proportionate to the length of a complementary sequence. Meanwhile, if the length of a primer increases, the length of a target nucleic acid to be amplified shortens. Therefore, there is still a need to develop a polynucleotide that is specifically and stably binding to a target nucleic acid and increases the length of an amplified target nucleic acid.

BRIEF SUMMARY OF THE INVENTION

Provided are polynucleotides for efficiently amplifying target nucleic acids. The polynucleotide comprises at least two complementary regions that are complementary to a target nucleic acid.

Provided are compositions and kits including the polynucleotides for efficiently amplifying target nucleic acids. The composition and kits comprise (a) a target nucleic acid; and (b) a first polynucleotide comprising at least two complementary regions that are complementary to the target nucleic acid. Provided are methods of efficiently producing a nucleotide sequence complementary to a target nucleic acid. The methods comprise (a) hybridizing a target nucleic acid with a first polynucleotide comprising at least two complementary regions that are complementary to a target nucleic acid to form a hybridized product and (b) incubating the hybridized product in the presence of a nucleic acid polymerase to extend a nucleotide sequence complementary to the target nucleic acid from the 3'-terminal of the polynucleotide.

In the polypeptides, compositions, kits, and methods, a first complementary region of the polypeptide comprises at least one consecutive nucleotide from the 3'-terminal thereof that is complementary to the target nucleic acid. At least one second complementary region of the polypeptide comprises at least one consecutive nucleotide at the 5'-terminal side of the first complementary region, which is complementary to the target nucleic acid. The first complementary region is hybridizable to nucleotides which are present at the 3'-terminal side of the second complementary region based on the order of nucleotides of the target nucleic acid.

DESCRIPTION OF THE SEVERAL VIEWS OF THE DRAWINGS

These and/or other aspects will become apparent and more readily appreciated from the following description of the embodiments, taken in conjunction with the accompanying drawings of which:

FIG. 1A is a schematic diagram of a first polynucleotide, a second polynucleotide and a target nucleic acid.

FIG. 1B is an schematic diagram showing a method of preparing a nucleotide sequence complementary to the target nucleic acid by using the first polynucleotide and the second nucleotide.

DETAILED DESCRIPTION OF THE INVENTION

Figure 2:
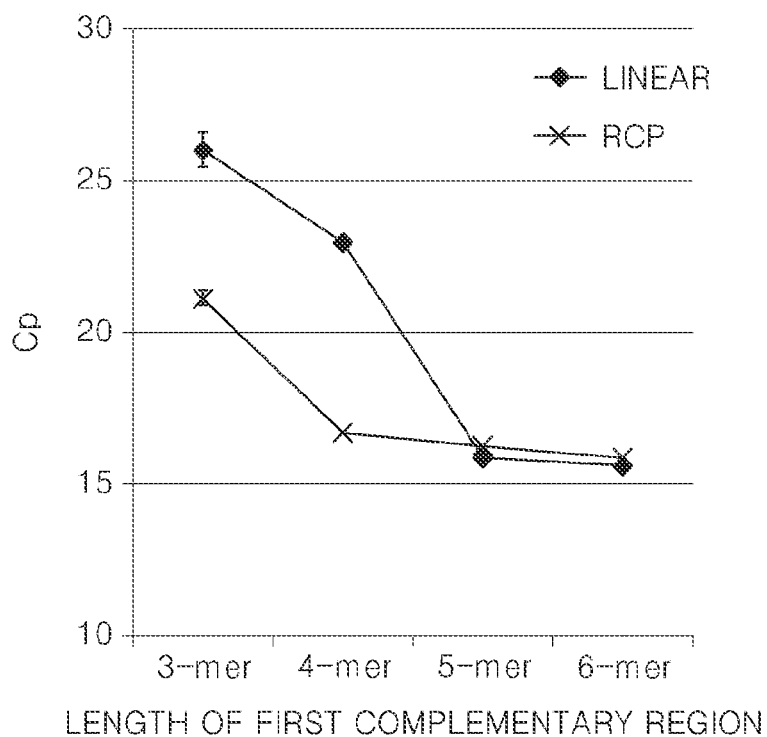
FIG. 2 is a graph showing an effect of the length of a first complementary region (x-axis) on extension efficiency (cross-point value (Cp), y-axis), according to an embodiment of the present invention.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an embodiment of the present invention, there is a first polynucleotide including at least two regions that are complementary to a target nucleic acid (herein referred to as "complementary regions"). The first complementary region of the at least two complementary regions includes at least one consecutive nucleotide from the 3'-terminal thereof that is complementary to the target nucleic acid. The at least one second complementary region of the at least two complementary regions includes at least one consecutive nucleotide at the 5'-terminal side of the first complementary region, which is complementary to the target nucleic acid. The first complementary region is hybridizable to nucleotides which are present at the 3'-terminal side of the second complementary region based on the order of nucleotides of the target nucleic acid.

The first complementary region of the first polynucleotide may be complementary to at least one consecutive nucleotide from the 3'-terminal of the target nucleic acid, including the 3'-terminal nucleotide of the target nucleic acid. For example, the first complementary region may be complementary to at least two consecutive nucleotides from the 3'-terminal of the target nucleic acid, including the 3'-terminal nucleotide of the target nucleic acid. For example, the first complementary region may have consecutive nucleotides complementary to 2 to 50, 2 to 40, 2 to 30, 2 to 20, 2 to 10, 3 to 50, 4 to 40, 3 to 30, 3 to 20, 3 to 10, or 3 to 16 (e.g., 4, 5, 6, 7, 8, 9, 10, 11, 12, 13, 14, or 15) consecutive nucleotides of the target nucleic acid, including the 3'-terminal nucleotide of the target nucleic acid.

The second complementary region of the polynucleotide may be complementary to at least one consecutive nucleotide from the 5'-terminal of the target nucleic acid. For example, the second complementary region may be complementary to at least one consecutive nucleotide from the 5'-terminal of the target nucleic acid, including the 5'-terminal nucleotide of the target nucleic acid. For example, the at least one consecutive nucleotide may be 1 nucleotide (hereinafter, referred to as "nt") to 50 nt, for example, 1 nt to 40 nt, 1 nt to 30 nt, 1 nt to 20 nt, 1 nt to 10 nt, 2 nt to 40 nt, 2 nt to 30 nt, 2 nt to 20 nt, 2 nt to 10 nt, 3 nt to 40 nt, 3 nt to 30 nt, 3 nt to 20 nt, or 3 nt to 10 nt (e.g., 4 nt, 5 nt, 6 nt, 7 nt, 8 nt, or 9 nt).

In this regard, the second complementary region may be complementary to at least two consecutive nucleotides of the target nucleic acid. For example, the second complementary region may have consecutive nucleotides complementary to 2 to 50, 2 to 40, 2 to 30, 2 to 20, 2 to 10, 3 to 50, 4 to 40, 3 to 30, 3 to 20, 3 to 10, or 3 to 16 (e.g., 4, 5, 6, 7, 8, 9, 10, 11, 12, 13, 14, or 15) consecutive nucleotides of the target nucleic acid, including the 5'-terminal nucleotide of the target nucleic acid.

In one embodiment, at least three consecutive nucleotides of the second complementary region may be complementary to the target nucleic acid. For example, the at least three consecutive nucleotides may be 3 nt to 50 nt, 3 nt to 40 nt, 3 nt to 30 nt, 3 nt to 20 nt, 3 nt to 10 nt, or 4 nt to 16 nt.

The first polynucleotide may include 1 to 3, for example, 1, 2, or 3, second complementary region(s).

In the first polynucleotide, the first complementary region and the second complementary region may be separated from each other by at least one nucleotide. In one embodiment, the first complementary region and the second complementary region may be separated from each other by a linker. The linker may be, for example, a nucleic acid, a nucleic acid variant, protein, carbohydrate, lipid molecules, or a combination thereof. The nucleic acid variant may be peptide nucleic acid (PNA), locked nucleic acid (LNA), or a combination thereof. For example, the linker may include a nucleic acid having 0 to 50 nt. The length of the linker may be, for example, 1 nt to 50 nt, 2 nt to 50 nt, 2 nt to 40 nt, 2 nt to 30 nt, 2 nt to 20 nt, 2 nt to 10 nt, 3 nt to 50 nt, 4 nt to 40 nt, 3 nt to 30 nt, 3 nt to 20 nt, 3 nt to 10 nt, or 4 nt to 10 nt (e.g., 5 nt, 6 nt, 7 nt, 8 nt, or 9 nt). In one embodiment, the linker may be a primer binding site, a restriction enzyme recognition site, a probe binding site, or a combination thereof.

The first polynucleotide may be DNA or RNA. Also, examples of the polynucleotide include nucleotide analogues, for example, PNA and LNA. For example, the second complementary region of the polynucleotide may include a nucleotide analogue, for example, PNA, LNA, or a combination thereof. The nucleotide analogue, for example, PNA, LNA, or a combination thereof, may also be included in the first complementary region. The polynucleotide may be single-stranded. The length of the polynucleotide may be 7 nt to 200 nt, 7 nt to 180 nt, 7 nt to 150 nt, 7 nt to 130 nt, 7 nt to 100 nt, 7 nt to 80 nt, 7 nt to 50 nt, 7 nt to 30 nt, 7 nt to 20 nt, 7 nt to 15 nt, or 10 nt to 40 nt (e.g., 15 nt, 20 nt, 25 nt, 30 nt, or 35 nt).

The target nucleic acid may be DNA, RNA, or a chimera of DNA and RNA. The target nucleic acid may be single-stranded or double-stranded. The length of the target nucleic acid may be 20 nt to 200 nt, 20 nt to 180 nt, 20 nt to 150 nt, 20 nt to 130 nt, 20 nt to 100 nt, 20 nt to 80 nt, 20 nt to 50 nt, 20 nt to 30 nt, or 20 nt to 40 nt. The target nucleic acid may be small RNA (e.g., natural small RNA). For example, the small RNA may be microRNA, siRNA, tRNA, or a combination thereof. In addition, the target nucleic acid, which may be RNA having at least 200 nucleotides, may be RNA having a region where a sequence of 30 consecutive nucleotides has a GC content of less than 30% (e.g., less than 25%, less than 20%, less than 15%, less than 10%, or less than 5%) or of at least 80% (e.g., at least 85%, at least 90%, or at least 95%), RNA including at least 5 consecutive nucleotides having complementary sequences in molecules so as to form an intramolecular secondary structure, RNA including at least 5 consecutive nucleotides that are complementary to each other, or a combination thereof.

The first and second complementary regions of the polynucleotide may be hybridized to the target nucleic acid, being spaced apart from each other by at least 1 nt. For example, the first and second complementary regions may be spaced apart from each other by 1 nt to 20 nt, 1 nt to 10 nt, 1 nt to 5 nt, 2 nt, 3 nt, 4 nt, 5 nt, 6 nt, 7 nt, 8 nt, 9 nt, 10 nt, or 11 nt.

According to another embodiment of the present invention, there is provided a second polynucleotide including a third complementary region complementary to the first polynucleotide. The third complementary region may be complementary to at least one consecutive nucleotide separated from the first complementary region of the first polynucleotide.

The third complementary region may be at least one consecutive nucleotide starting from a location separated by about 0 to about 20 nt, from the first complementary region of the first polynucleotide. For example, the third complementary region may be complementary to at least one consecutive nucleotide starting from a location spaced apart by 0 nt, 1 nt, 2 nt, 3 nt, 4 nt, 5 nt, 6 nt, 7 nt, 8 nt, 9 nt, 10 nt, about 11 to about 15 nt or about 11 to about 20 nt from the first complementary region of the first polynucleotide.

The second polynucleotide may have a length of about 2 to about 100 nt. For example, the second polynucleotide may have a length of about 2 to about 80 nt, about 2 to about 60, about 2 to about 40, about 2 to about 20 nt, about 4 to about 18 nt, about 6 to about 16 nt, or about 8 to about 14 nt.

The second polynucleotide may include DNA, RNA, PNA, LNA, nucleotide analogues or a combination thereof. The third complementary region of the second polynucleotide may include DNA, RNA, PNA, LNA, nucleotide analogues or a combination thereof. Also, the second polynucleotide may be single stranded.

The 3'-terminal of the second polynucleotide may be modified. The 3'-terminal of the second polynucleotide, for example, may include an inverted nucleotide, dideoxynucleotide, amine group, alkyl chain moiety or a combination thereof. The modified 3'-terminal may prevent the target nucleic acid from acting as a primer.

The first and second polynucleotides have multiple uses. For example, the first polynucleotide may act as a primer in template-dependent nucleic acid synthesis. Thus, the first polynucleotide may be used as a primer. The first polynucleotide may also be used as a probe for confirming a presence of the target nucleic acid in a sample. The second polynucleotide may be used as a clamp in a template-dependent nucleic acid synthesis to improve efficiency and specificity of a reverse transcription.

According to another embodiment of the present invention, there is provided a composition and kit for amplifying a target nucleic acid. The composition and kit include a target nucleic acid, and a first polynucleotide including at least two complementary regions that are complementary to the target nucleic acid.

The composition and kit may further include the second polynucleotide including a third complementary region complementary to the first polynucleotide. The third complementary region may be complementary to at least one consecutive nucleotide separated from the first complementary region of the first polynucleotide.

The composition and kit may be used for amplifying the target nucleic acid. The amplification process may be performed using one of various known methods of amplifying nucleic acids. The amplification of the target nucleic acid may be DNA amplification or RNA amplification. The amplification process may be performed under thermal cycling or isothermal conditions. Examples of the amplification method include a polymerase chain reaction (PCR), nucleic acid sequence-based amplification (NASBA), a ligase chain reaction (LCR), strand displacement amplification (SDA), rolling circle amplification (RCA), and the like. Also, the amplification method may include a method of amplifying RNA. For example, the amplification method may include reverse transcription (RT) or RT-PCR. The amplification process may be a process of increasing the copy number of target nucleic acid sequences or sequences complementary thereto. The term "PCR" used herein refers to a method of amplifying a target nucleic acid from primer pairs specifically binding to the target nucleic acid by using a polymerase.

Thus, the composition and kit may further include a material known for the amplification of the target nucleic acid. For example, the composition and kit may further include a nucleic acid polymerase, a buffer for the activity of the nucleic acid polymerase, a cofactor, and/or a matrix. The nucleic acid polymerase may be one selected from a DNA polymerase, a RNA polymerase, a reverse transcriptase, and a combination thereof. The term "reverse transcription" may refer to the synthesis of DNA strands that are complementary to RNA sequences by using RNA as a template. The nucleic acid polymerase may have strand displacement activity. For example, the nucleic acid polymerase may be at least one reverse transcriptase derived from retrovirus, for example, HIV (Human Immunodeficiency Virus), MMLV (Moloney Murine Leukemia Virus), or AMV (Avian Myeloblastosis Virus). The nucleic acid polymerase may not have 3'→5' exonuclease activity. The composition and kit may include a material for reverse transcription or PCR amplification. The composition and kit may further include an instruction manual used to amplify the target nucleic acid.

According to another embodiment of the present invention, there is provided a method of producing a nucleotide sequence complementary to a target nucleic acid, the method including (a) hybridizing the target nucleic acid with a first polynucleotide including at least two complementary regions that are complementary to the target nucleic acid to form a hybridized product and (b) incubating the hybridized product in the presence of a nucleic acid polymerase to extend a nucleotide sequence complementary to the target nucleic acid from the 3'-terminal of the first polynucleotide.

The hybridization process may be performed using one of various known methods. For example, the hybridization process may be performed by incubating the first polynucleotide and the target nucleic acid in a known buffer appropriate for the hybridization of nucleic acids. The hybridization process may be performed at a temperature ranging from about 0° C. to about 25° C., for example, 4° C. The hybridization temperature may be appropriately adjusted according to the sequences and lengths of selected first polynucleotide and target nucleic acid. The hybridization process may be performed for an appropriate time period, for example, about 1 to about 12 hours (overnight).

The method includes incubating the hybridized product in the presence of a nucleic acid polymerase to extend a nucleotide sequence complementary to the target nucleic acid from the 3'-terminal of the polynucleotide.

The incubating process may be performed under conditions appropriate for the activity of the nucleic acid polymerase. The incubating process may be performed in the presence of the nucleic acid polymerase, a buffer for the activity of the nucleic acid polymerase, a cofactor, and a substrate for the enzymes. The nucleic acid polymerase may be one selected from a DNA polymerase, a RNA polymerase, a reverse transcriptase, and a combination thereof. The term "reverse transcription" may refer to the synthesis of DNA strands that are complementary to RNA sequences by using RNA as a template. The nucleic acid polymerase may have strand displacement activity. For example, the nucleic acid polymerase may be a reverse transcriptase derived from retrovirus, for example, HIV, MMLV, or AMV. The nucleic acid polymerase may not have 3'→5' exonuclease activity. For example, the incubating process may be performed in the presence of a material for RT or PCR amplification.

Via the incubating process, the nucleotide sequence complementary to the target nucleic acid may be extended from the 3'-terminal of the first polynucleotide. The extending process includes extending from the 3'-terminal of the first polynucleotide, with the nucleic acid polymerase displacing the 5'-terminal of the first polynucleotide hybridized with the target nucleic acid.

The method may further include hybridizing a hybridized product and a second polynucleotide. The second polynucleotide may be a polynucleotide including a third complementary region complementary to the first polynucleotide. The third complementary region may be complementary to at least one consecutive nucleotide separated from the first complementary region of the first polynucleotide.

Regarding the method, hybridizing the first polynucleotide and the target nucleic acid, and hybridizing the hybridized product and the second polynucleotide may be performed simultaneously or consecutively. For example, the target nucleic acid and the first polynucleotide may be hybridized and then the hybridized product and the second polynucleotide may be hybridized; the first polynucleotide and the second polynucleotide may be hybridized and then the hybridized product and the target nucleic acid may be hybridized; or the first polynucleotide, the second polynucleotide, and the target nucleic acid may be hybridized simultaneously.

The method may further include determining whether or not the produced product, i.e., the nucleotide sequence complementary to the target nucleic acid, is present. The method may further include determining that, as a result of the above-described determination, if the produced product is present, the target nucleic acid exists in a sample, and on the other hand, if the produced product is not present, the target nucleic acid does not exist in the sample.

In addition, the method may further include amplifying a nucleic acid by using as a template the produced product, i.e., the nucleotide sequence complementary to the target nucleic acid. The amplification process may be performed using one of various known methods as described herein.

The method may further include determining whether or not the amplified product, i.e., the nucleotide sequence complementary to the target nucleic acid, is present. The method may further include determining that, as a result of the above-described determination process, if the amplified product is present, the target nucleic acid exists in a sample, and on the other hand, if the amplified product is not present, the target nucleic acid does not exist in the sample.

The method may include hybridizing a target nucleic acid with a polynucleotide including at least two complementary regions that are complementary to the target nucleic acid, wherein a first complementary region of the at least two complementary regions includes at least one nucleotide sequence mismatched with a sequence of the target nucleic acid and at least one consecutive nucleotide from the 3'-terminal of the polynucleotide, which is complementary to the target nucleic acid, and at least one second complementary region of the at least two complementary regions includes at least one consecutive nucleotide at the 5'-terminal side of the first complementary region, which is complementary to the target nucleic acid, wherein the first complementary region is located at the 5'-terminal side of the second complementary region, based on the order of nucleotides of the target nucleic acid.

The first complementary region may include 1 to 4 nt mismatches, for example, 1, 2, 3, or 4 nt mismatch(es). The mismatch may be one nucleotide mismatch located at a $1^{st}$, $2^{nd}$, $3^{rd}$, $4^{th}$, $5^{th}$, or $6^{th}$ position from the 3'-terminal of the first complementary region. The method may further include comparing a product extended by using the polynucleotide containing the mismatch with a product extended by using the polynucleotide not including the mismatch.

In addition, the method may further include determining whether or not mutation is present in the target nucleic acid based on the comparison results. For example, the method may further include determining that if a product extended from the polynucleotide including the mismatch is obtained, but a product extended from the polynucleotide not including the mismatch is not obtained, a nucleotide of the target nucleic acid that corresponds to the mismatch has a mutation. Also, the method may further include determining that if a product extended from the polynucleotide including the mismatch is not obtained, but a product extended from the polynucleotide not including the mismatch is obtained, a nucleotide of the target nucleic acid that corresponds to the mismatch has no mutation.

FIGS. 1A and B illustrate a method of preparing a nucleotide sequence complementary to a target nucleic acid using a first polynucleotide and a second polynucleotide, according to an embodiment of the present invention. As shown in FIGS. 1A and B, the target nucleic acid A includes a 5'-terminal region A1, a middle region A2, and a 3'-terminal region A3. The first polynucleotide B includes the first complementary region B3 complementary to the 3'-terminal region A3 of the target nucleic acid, a non-complementary region B2 to the target nucleic acid, and the second complementary region B1 complementary to 5'-terminal region A1 of the target nucleic acid. A region non-complementary to the target nucleic acid B2 includes a region complementary B2-1 to the third complementary region C1 of the second polynucleotide C. The second polynucleotide C includes a third complementary region C1 and the 3'-terminal thereof may be a modified nucleotide C2. The third complementary region C1 of the second polynucleotide may be separated from the first polynucleotide by at least one nucleotide at a 3'-terminal of a region non-complementary B2 to the target nucleic acid. A hybridization of the first polynucleotide, the second polynucleotide and the target nucleic acid facilitates an efficient reverse transcription by a reverse transcriptase because the third complementary region C1 of the second polynucleotide is arranged in the 3'-terminal direction from the target nucleic acid A. When the reverse transcription is completed, a cDNA D is produced, including cDNA D1 at the 5'-terminal region A1 of the target nucleic acid, and cDNA D2 in the middle region A2 of the target nucleic acid.

Since the first complementary region (B3) and the second complementary region (B1) are complementary to the target nucleic acid (A), they synergically contribute to the hybridization, and thus may synergically contribute to the stabilization of the hybridized product. Therefore, the length of the first complementary region, which contributes to the priming of nucleic acid amplification, may be shortened without loss of specificity, sensitivity, and/or a speed of amplification. In addition, when the 3'-terminal of the polynucleotide is extended by a nucleic acid polymerase (refer to D of FIG. 1), the target nucleic acid may be amplified. In FIG. 1B, the extension of the 3'-terminal of the polynucleotide includes reverse transcription or synthesis of DNA strands from DNA strands. The first and second complementary regions hybridized with the target nucleic acid may be spaced apart from each other by at least 1 nt. Also, the second polynucleotide may be decreased a length of the first complementary region used for priming, such that a length of the reverse transcribed product may be lengthened, PCR primer design may be easier, and the specificity of the reverse transcription may be increased.

EXAMPLES

One or more embodiments of the present invention will now be described more fully with reference to the following examples. However, these examples are provided only for illustrative purposes and are not intended to limit the scope of the invention.

Example 1

Preparation of Reverse Transcription Primer and Clamp

A sequence complementary to a target nucleic acid was extended from the 3'-terminal of a first polynucleotide (hereinafter, referred to as "reverse transcription primer," "RT primer," or "RTP") including at least two complementary regions that are complementary to a target nucleic acid, wherein a first complementary region of the at least two complementary regions includes at least one consecutive nucleotide from the 3'-terminal thereof that is complementary to the target nucleic acid, wherein at least one second complementary region of the at least two complementary regions includes at least one consecutive nucleotide at the 5'-terminal side of the first complementary region, which is complementary to the target nucleic acid, and wherein the first complementary region is located at the 5'-terminal side of the second complementary region, based on the order of nucleotides of the target nucleic acid. As a control, a general primer having no reverse configuration (hereinafter, referred to as "linear primer) was used. The "reverse transcription primer" may be reciprocally exchanged with the "reverse configuration primer." The first complementary region of the RTP is referred to as a "priming region," and the second complementary region of the RTP is referred to as an "adaptor region" or an "adaptor."

Also, a second polynucleotide (hereinafter, "clamp" or "clamp nucleotide") including a third complementary region complementary to the RTP was prepared, wherein the clamp has the third complementary region complementary to one or more consecutive nucleotides separated from the first complementary region of the RTP.

Example 2

Effect of Length of First Complementary Region on Extension Efficiency

An extension reaction of the RTP was performed by varying the length of the first complementary region from a 3mer to a 7mer. Reverse transcription was performed as the extension reaction.

Superscript III™ (Invitrogen) was used as a reverse transcriptase. The reverse transcription was performed by incubating the RTP and a RNA template in 50 mM Tris-HCl (pH 8.3 at room temperature) containing 37.5 mM KCl, 3 mM MgCl$_2$, and 10 mM DTT at 42° C. for 1 hour. As the RNA template, miR-16 RNA having a sequence of SEQ ID NO: 9 with a 20 nt tag sequence added to the 5'-terminal thereof was used. The Superscript III™ reverse transcriptase was a variant of Moloney murine leukemia virus (M-MLV) reverse transcriptase manipulated to have decreased RNA H activity and increased thermal stability.

The extended product was amplified by PCR. The PCR was performed by adding 50 nM of each of a primer pair and the extended product to a 2×SYBR RT-PCR master mixture (Exiqon) and thermally cycling the resulting mixture. The thermally cycling process was performed under the following conditions: 95° C. for 10 minutes, and 45 cycles, each cycle at 95° C. for 15 seconds, and at 60° C. for 1 minute. Next, melting curve analysis was performed by 5 measurement/° C. RT primers used were RTP-3mer (SEQ ID NO: 1), RTP-4mer (SEQ ID NO: 2), RTP-timer (SEQ ID NO: 3), RTP-7mer (SEQ ID NO: 4), RTP-3mer (SEQ ID NO: 5), Linear-4mer (SEQ ID NO: 6), Linear-timer (SEQ ID NO: 7), and Linear-7mer (SEQ ID NO: 8). The PCR primers used were a forward primer (SEQ ID NO: 10) and a reverse primer (SEQ ID NO: 11).

FIG. 2 is a graph showing an effect of the length of a first complementary region on extension efficiency. As illustrated in FIG. 2, when the length of the first complementary region is a 3mer and 4mer, the RTP had a significantly decreased Cp value as compared to the linear primer correlating with increased extension efficiency. When the length of the first complementary region is a 4mer, the Cp value of the RTP was 6.3 smaller than that of the control.

Example 3

Effects of Reaction Temperature and Primer Concentration on Extension Efficiency The target nucleic acid was amplified using the RTP having a length of a 6mer having a little difference in extension efficiency from that of the control. The RTP and the control had sequences of SEQ ID NOS: 12 and 13, respectively, and a target RNA (miR-3141 RNA with a 20 nt tag sequence added to the 5'-terminal thereof) had a sequence of SEQ ID NO: 14. The concentrations of the RTP used were 1 nM, 10 nM, and 100 nM, respectively, and reverse transcription temperatures used were 42° C., 50° C., and 55° C., respectively. The reverse transcription and PCR conditions except for the conditions listed above were the same as those described in Example 1 above.

Figure 3:
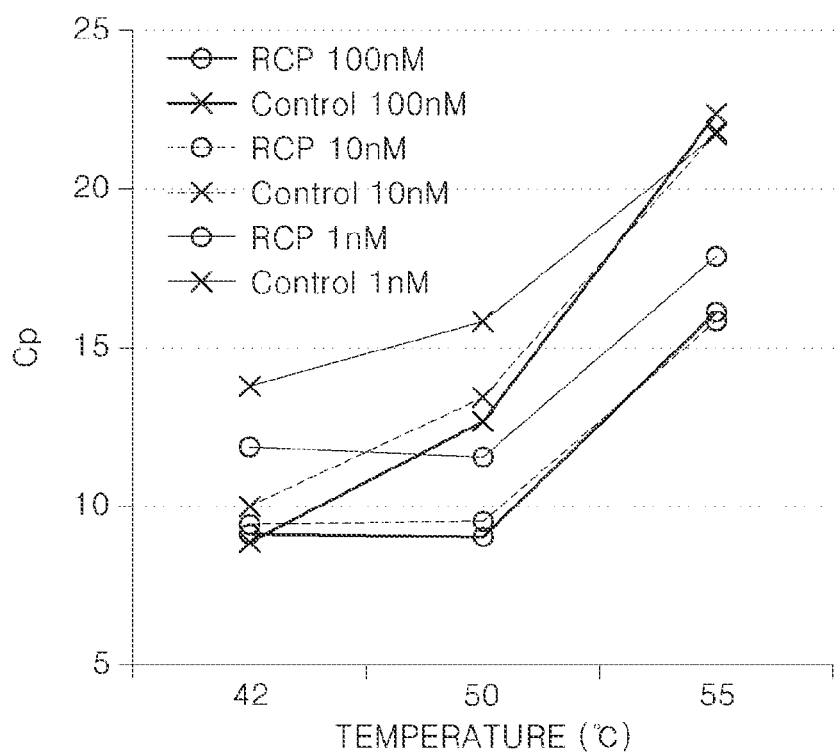
FIG. 3 is a graph showing effects of a reaction temperature (° C.; x-axis) and a primer concentration on extension efficiency (Cp; y-axis) of the 3'-terminal of a reverse transcription primer (RTP) by reverse transcription, according to an embodiment of the present invention.

FIG. 3 is a graph showing effects of a reaction temperature and a primer concentration on extension efficiency of the 3'-terminal of the RTP by reverse transcription. As illustrated in FIG. 3, the RTP had decreased Cp values as compared to the control.

Example 4

Effect of Length of Second Complementary Region on Extension Efficiency

The effect of the length of the second complementary region on extension efficiency of the RTP in transcription and PCR amplification was confirmed.

As target RNAs, miR-16 with a 20 nt tag sequence added to the 5'-terminal thereof (SEQ ID NO: 9) and miR-3141 with a 20 nt tag sequence added to the 5'-terminal thereof (SEQ ID NO: 14) were used. The RTPs used with respect to miR-3141 were RTPs with second complementary regions having lengths of 4mer, 8mer, 10mer, 12mer, 14mer, and 15mer that are respectively added to the 5'-terminal thereof and complementary to the target RNA (SEQ ID NOS: 15, 16, 17, 18, 19, and 20, respectively). The RTPs used with respect to miR-16 were RTPs with second complementary regions having lengths of 4mer, 8mer, 10mer, 12mer, 14mer, and 16mer that are respectively added to the 5'-terminal thereof and complementary to the target RNA (SEQ ID NOS: 21, 22, 23, 24, 25, and 26, respectively).

Figure 4:
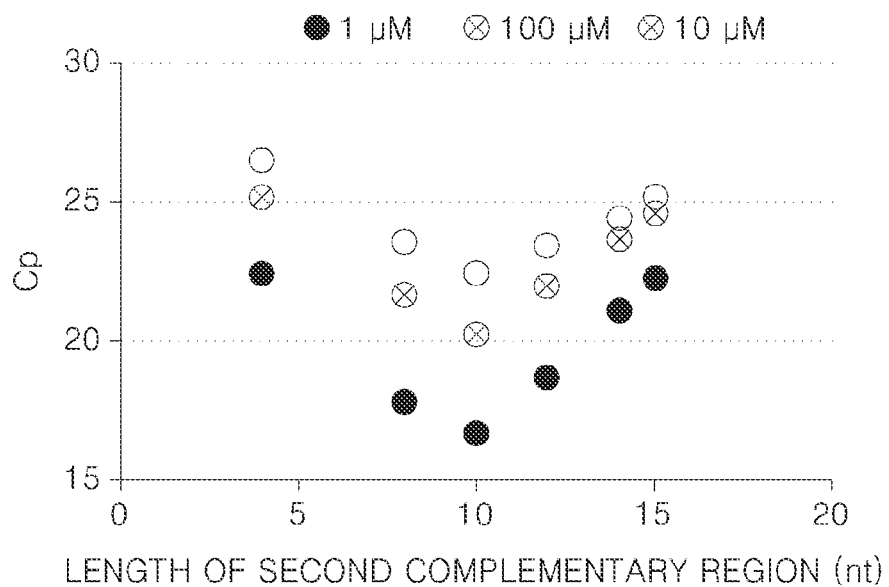
FIG. 4 is a graph showing the effect of the length of a second complementary region (nucleotides (nt); x-axis) on extension efficiency (Cp; y-axis) when miR-3141 is used as a target nucleic acid, according to an embodiment of the present invention.

FIG. 4 is a graph showing an effect of the length of a second complementary region on extension efficiency when miR- 3141 is used as a target nucleic acid. As shown in FIG. 4, the RTP including the second complementary region having a length of 10mer had the lowest Cp value.

Figure 5:
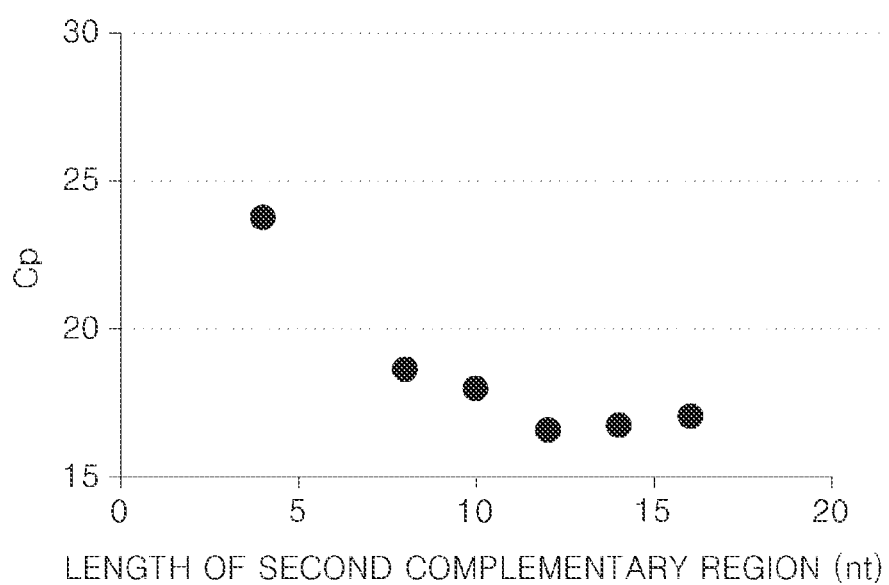
FIG. 5 is a graph showing the effect of the length of a second complementary region (nucleotides (nt); x-axis) on extension efficiency (Cp; y-axis) when miR-16 is used as a target nucleic acid, according to an embodiment of the present invention.

FIG. 5 is a graph showing an effect of the length of a second complementary region on extension efficiency when miR-16 is used as a target nucleic acid. As shown in FIG. 5, the RTP including the second complementary region having a length of 12mer had the lowest Cp value.

Table 1 (miR-3141) and Table 2 (miR-16) show characteristics of the second complementary region with the reverse transcription primers (RTPs).

A primer having no mismatch sequence and having a sequence complementary to the target nucleic acid (hereinafter, referred to as "wild-type (WT)") and primers having mismatch sequences that correspond to the $1^{st}$, $2^{nd}$, $3^{rd}$, $4^{th}$, $5^{th}$, and $6^{th}$ positions, respectively, from the 3'-terminal of miR-3141 (M1, M2, M3, M4, M5, and M6, respectively) were used. In this regard, first complementary regions having the lengths of 0mer, 1mer, 2mer, 3mer, 4mer, and 6mer were used. When the length of the first complementary region is a 6mer, the WT primer and the M1, M2, M3, M4, M5 and M6 primers have sequences of SEQ ID NOS: 27, 28, 29, 30, 31,

TABLE 1

| SEQ ID NO. of RTP | Length of second complementary region in RTP | Sequence of second complementary region in RTP | GC content (%) | basic Tm (° C.) | Salt concentration-adjusted Tm (° C.) | NN Tm (° C.) |
| --- | --- | --- | --- | --- | --- | --- |
| SEQ ID NO. 15 | 4 | CCTC (SEQ ID NO: 172) | 3 | 14 | 14 | — |
| SEQ ID NO. 16 | 8 | CCGCCCTC (SEQ ID NO: 173) | 7 | 30 | 30 | 18.73 |
| SEQ ID NO. 17 | 10 | ACCCGCCCTC (SEQ ID NO: 174) | 8 | 36 | 36 | 31.49 |
| SEQ ID NO. 18 | 12 | CCACCCGCCCTC (SEQ ID NO: 175) | 10 | 44 | 44 | 40.98 |
| SEQ ID NO. 19 | 14 | CTCCACCCGCCCTC (SEQ ID NO: 176) | 11 | 49.1 | 52.7 | 46.58 |

TABLE 2

| SEQ ID NO. of RTP | Length of second complementary region in RTP | Sequence of second complementary region in RTP | GC content (%) | basic Tm (° C.) | Salt concentration-adjusted Tm (° C.) | NN Tm (° C.) |
| --- | --- | --- | --- | --- | --- | --- |
| SEQ ID NO. 21 | 4 | TGCT (SEQ ID NO: 177) | 2 | 12 | 12 | — |
| SEQ ID NO. 22 | 8 | GTGCTGCT (SEQ ID NO: 178) | 5 | 26 | 26 | 8.98 |
| SEQ ID NO. 23 | 10 | ACGTGCTGCT (SEQ ID NO: 179) | 6 | 32 | 32 | 28.32 |
| SEQ ID NO. 24 | 12 | TTACGTGCTGCT (SEQ ID NO: 180) | 6 | 36 | 36 | 33.97 |
| SEQ ID NO. 25 | 14 | ATTTACGTGCTGCT (SEQ ID NO: 181) | 6 | 34.4 | 38 | 38.41 |
| SEQ ID NO. 26 | 16 | ATATTTACGTGCTGCT (SEQ ID NO: 182) | 6 | 38.3 | 43.2 | 41.29 |

In Tables 1 and 2, NN denotes nearest neighbor.

Example 5

Effect of First Complementary Region Including Nucleotide Sequence Mismatched with Target Nucleic Acid on Extension Efficiency An effect of a RTP including a first complementary region having a nucleotide sequence mismatched with a target nucleic acid sequence on extension efficiency in transcription and PCR amplification was confirmed.

32, and 33, respectively. As the target nucleic acid, miR-3141 RNA having a sequence of SEQ ID NO: 14 was used.

When the length of the first complementary region is a 4mer, the WT primer and the M1, M2, M3 and M4 primers have sequences of SEQ ID NOS: 34, 35, 36, 37, and 38, respectively.

When the length of the first complementary region is a 3mer, the WT primer and the M1, M2 and M3 primers have sequences of SEQ ID NOS: 39, 40, 41, and 42, respectively.

When the length of the first complementary region is a 2mer, the WT primer and the M1 and M2 primers have sequences of SEQ ID NOS: 43, 44, and 45, respectively.

When the length of the first complementary region is a 1 mer, the WT primer and the M1 primer have sequences of SEQ ID NOS: 46 and 47, respectively.

When the length of the first complementary region is a 0mer, the WT primer has a sequence of SEQ ID NO: 48.

The concentrations of each primer used were 10 nM, 100 nM, and 1 μM, respectively. The reverse transcription and PCR conditions, except for the condition described above, are the same as those described in Example 1 above.

Figure 6:
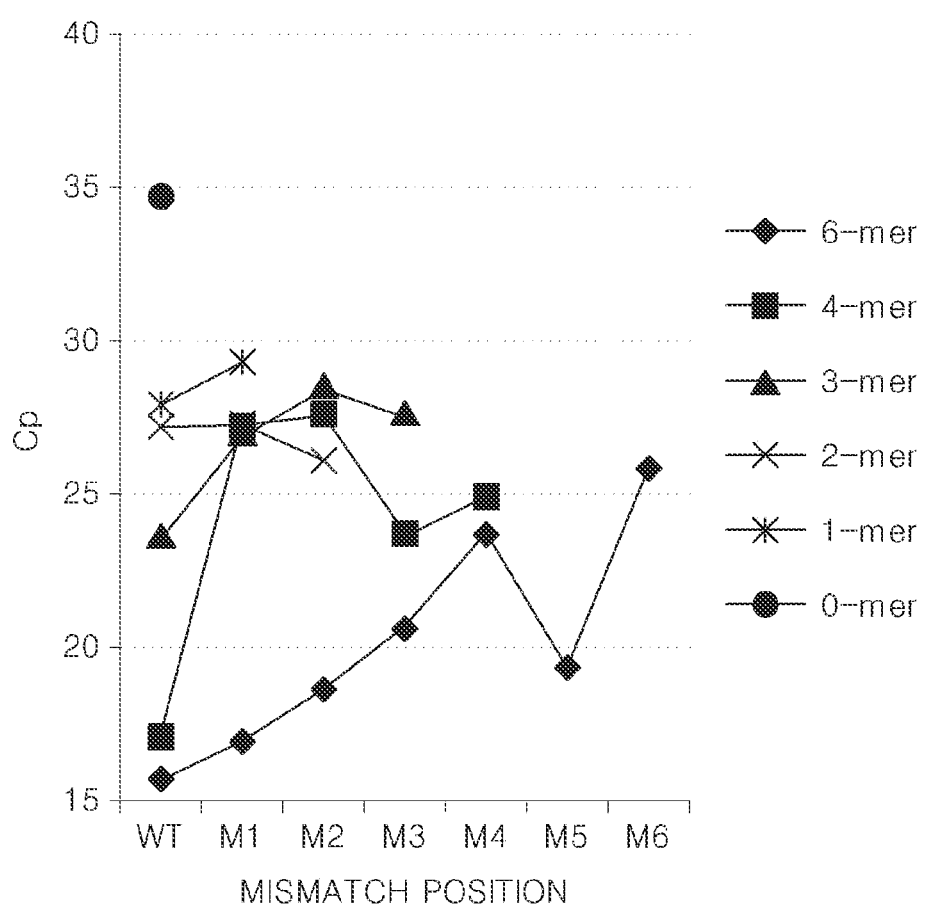
FIG. 6 is a graph showing the effect of a first complementary region having a nucleotide sequence mismatched with a sequence of a target nucleic acid, according to an embodiment of the present invention. The position of the mismatch is indicated on the x-axis and the extension efficiency (Cp) is indicated on the y-axis.
Figure 7:
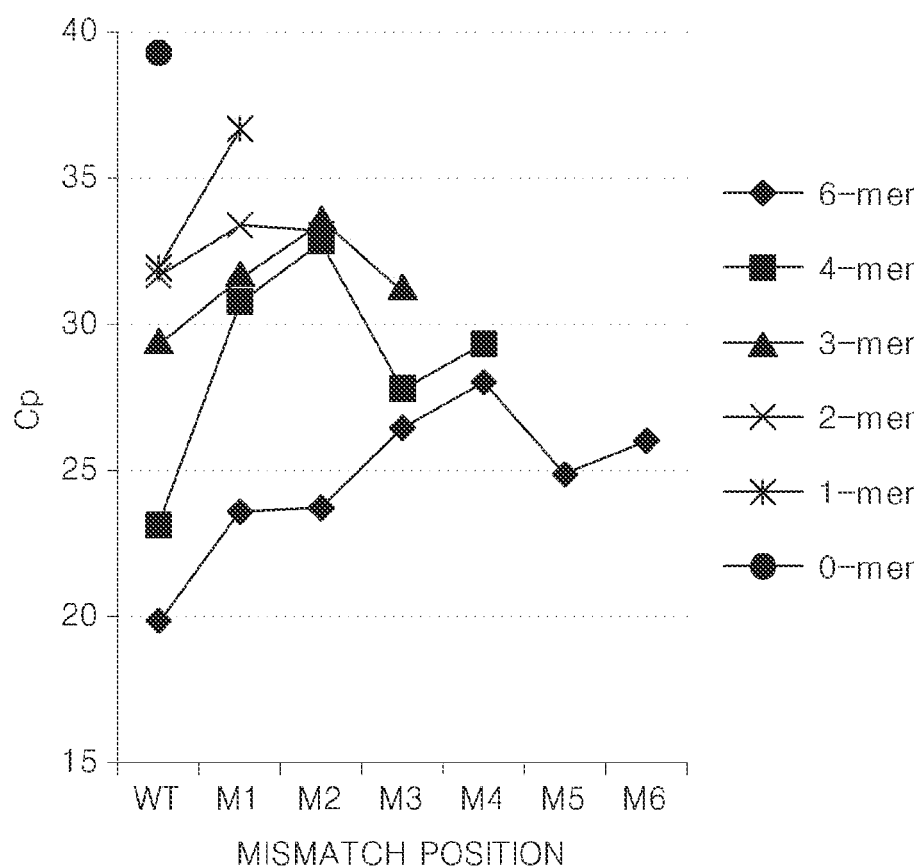
FIG. 7 is a graph showing the effect of a first complementary region having a nucleotide sequence mismatched with a sequence of a target nucleic acid, according to an embodiment of the present invention. The position of the mismatch is indicated on the x-axis and the extension efficiency (Cp) is indicated on the y-axis.
Figure 8:
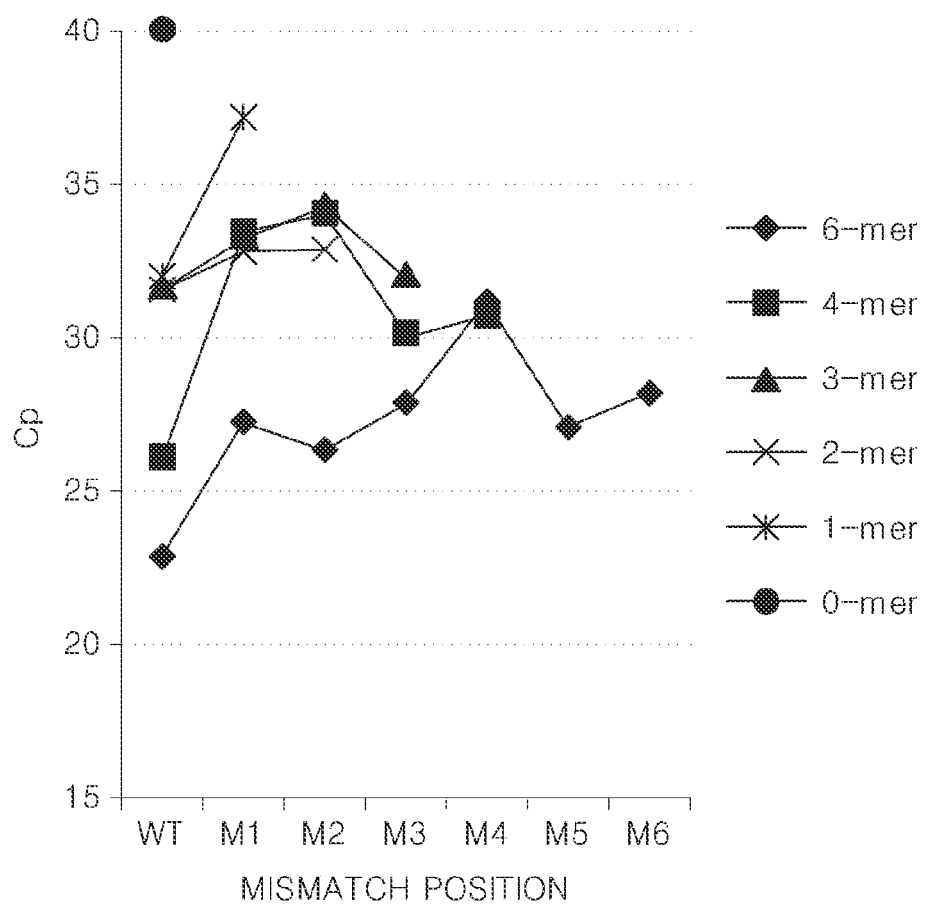
FIG. 8 is a graph showing the effect of a first complementary region having a nucleotide sequence mismatched with a sequence of a target nucleic acid, according to an embodiment of the present invention. The position of the mismatch is indicated on the x-axis and the extension efficiency (Cp) is indicated on the y-axis.

FIGS. 6 through 8 are graphs showing an effect of the first complementary region including a nucleotide sequence mismatched with a sequence of a target nucleic acid on extension efficiency. The concentrations of each primer illustrated in FIGS. 6 through 8 were 1 μM, 100 nM, and 10 nM, respectively. As shown in FIGS. 6 through 8, cross-point (Cp) values had a significant difference between the case where the first complementary region of the RTP had the mismatch sequence and the case where the first complementary region of the RTP did not have the mismatch sequence. Referring to FIGS. 6 through 8, when the length of the first complementary region is a 4mer, the Cp values of the mismatch primers were 6.8 to 10.7 greater than that of the WT primer. In FIGS. 6 through 8, M1, M2, M3, M4, M5, and M6 denote mismatch positions from the 3'-terminal of miR-3141 having a sequence of cggugagguc uuugguucau gagggcgggu ggag(M6) g(M5)a(M4)g(M3)g(M2)a(M1) (SEQ ID NO: 14).

Cp values represent the cycle by which the fluorescence of a sample increased to a level higher than the background fluorescence in the amplification cycle, and also represents the cycle in which a second derivative of the amplification curve has the maximum value. As extension efficiency is increased, the Cp value is decreased because the sample is amplified in less number of cycles.

The results of FIGS. 6 through 8 indicate that it may be confirmed whether or not mutation is present in the target nucleic acid by introducing a mismatch sequence to the first complementary region. Whether or not mutation is present in the target nucleic acid may be confirmed by comparing a product amplified from the mismatch primer with a product amplified from the primer having no mismatch sequence.

Example 6

Effect of Clamp and Clamp Length on Efficiency of Reverse Transcription

A reverse transcription reaction was performed by including a clamp or changing a clamp length to about a 6mer to about a 16mer.

Superscript III™ (Invitrogen) was used as a reverse transcriptase. The reverse transcriptase and a RNA template was incubated for an hour in 50 mM Tris-HCl, (pH 8.3 at a room temperature) containing 37.5 mM KCl, 3 mM $MgCl_2$, and 10 mM DTT, for an hour at 42° C. miR-16 (SEQ ID NO: 49) was used as the RNA template. Superscript III™ is an M-MLV (Moloney murine leukemia virus) reverse transcriptase variant engineered to reduce RNase H activity and to provide increased thermostability.

The resulting reverse transcription products were amplified by PCR. The PCR was performed by adding 50 nM of each primer, and reverse transcription products to a 2×SYBR RT-PCR master mixture (Exiqon) and thermal cycling thereof. The thermal cycling is performed 45 times, a cycling consisting of 10 minutes at 95° C., 15 seconds at 95° C., and 1 minute at 60° C. Subsequently, melting curve analysis was performed by 5 measurement/° C. Table 3 illustrates the sequences of the used template, a PCR primer, a reverse transcription primer, and a clamp. 'A0' as used in Table 3 refers to a linear primer.

TABLE 3

| | Name | Sequence |
|---|---|---|
| Template | miR16 | 5'-UAGCAGCACGUAAAUAUUGGCG-3' (SEQ ID NO: 49) |
| PCR primer | Forward primer | 5'-CGCGCTAGCAGCACGTAAAT-3' (SEQ ID NO: 50) |
| | Reverse primer | 5'-GTGCAGGGTCCGAGGT-3' (SEQ ID NO: 51) |
| RT primer | A12 RT0 | 5'-TACGTGCTGCTA GTGCAGGGTCCGAGGT ATTCGCACTGGATACGAC-3' (SEQ ID NO: 52) |
| | A12 RT1 | 5'-TACGTGCTGCTA GTGCAGGGTCCGAGGT ATTCGCACTGGATACGAC C-3' (SEQ ID NO: 53) |
| | A12 RT2 | 5'-TACGTGCTGCTA GTGCAGGGTCCGAGGT ATTCGCACTGGATACGAC CG-3' (SEQ ID NO: 54) |
| | A12 RT3 | 5'-TACGTGCTGCTA GTGCAGGGTCCGAGGT ATTCGCACTGGATACGAC CGC-3' (SEQ ID NO: 55) |
| | A12 RT4 | 5'-TACGTGCTGCTA GTGCAGGGTCCGAGGT ATTCGCACTGGATACGAC CGCC-3' (SEQ ID NO: 56) |
| | A12 RT6 | 5'-TACGTGCTGCTA GTGCAGGGTCCGAGGT ATTCGCACTGGATACGAC CGCCAA-3' (SEQ ID NO: 57) |
| | A0 RT0 | 5'-GTGCAGGGTCCGAGGT ATTCGCACTGGATACGAC-3' (SEQ ID NO: 58) |
| | A0 RT1 | 5'-GTGCAGGGTCCGAGGT ATTCGCACTGGATACGAC C-3' (SEQ ID NO: 59) |
| | A0 RT2 | 5'-GTGCAGGGTCCGAGGT ATTCGCACTGGATACGAC CG-3' (SEQ ID NO: 60) |
| | A0 RT3 | 5'-GTGCAGGGTCCGAGGT ATTCGCACTGGATACGAC CGC-3' (SEQ ID NO: 61) |
| | A0 RT4 | 5'-GTGCAGGGTCCGAGGT ATTCGCACTGGATACGAC CGCC-3' (SEQ ID NO: 62) |
| | A0 RT6 | 5'-GTGCAGGGTCCGAGGT ATTCGCACTGGATACGAC CGCCAA-3' (SEQ ID NO: 63) |

TABLE 3-continued

| Name | | Sequence |
|---|---|---|
| Clamp | C16 | 5'-GTCGTATCCAGTGCGA-3'<br>(SEQ ID NO: 64) |
| | C14 | 5'-GTCGTATCCAGTGC-3'<br>(SEQ ID NO: 65) |
| | C12 | 5'-GTCGTATCCAGT-3'<br>(SEQ ID NO: 66) |
| | C10 | 5'-GTCGTATCCA-3'<br>(SEQ ID NO: 67) |
| | C8 | 5'-GTCGTATC-3'<br>(SEQ ID NO: 68) |
| | C6 | 5'-GTCGTA-3'<br>(SEQ ID NO: 69) |

Figure 9A:
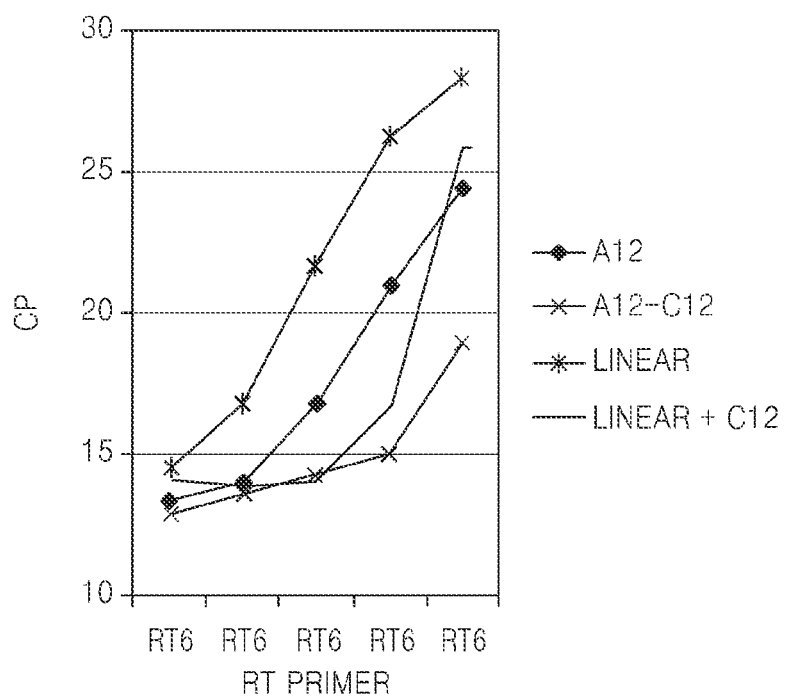
FIGS. 9A and 9B are graphs illustrating the effect of a clamp and a clamp length on the efficiency of a reverse transcription. The RT primer is indicated on the x-axis and the extension efficiency (Cp) is indicated on the y-axis.
Figure 9B:
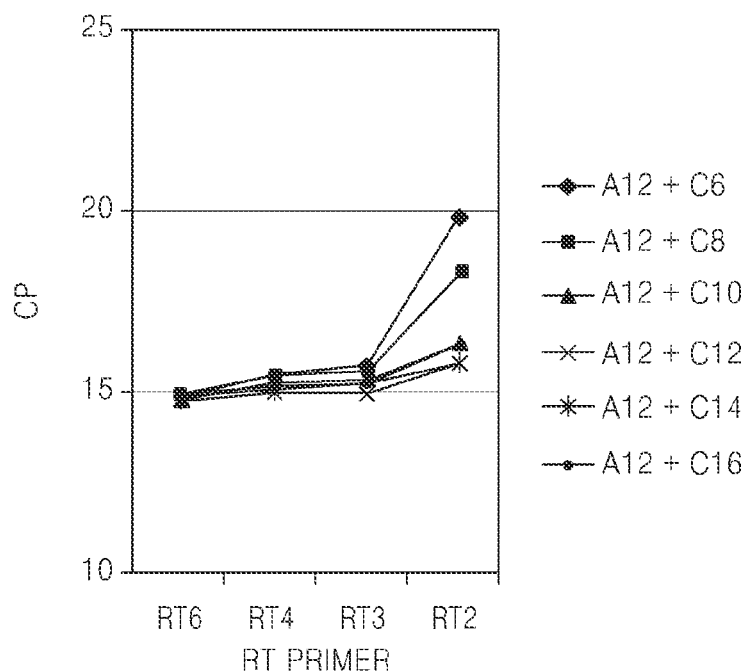

FIG. 9A illustrates an effect of a clamp on a reverse transcription efficiency, and FIG. 9B illustrates an effect of a clamp length on a reverse transcription efficiency. As shown in FIG. 9A, Cp value is reduced when the reverse transcription primer is used instead of the linear primer, and when the clamp is used, the Cp value decreased significantly. As shown in FIG. 9B, the Cp value decreased as the clamp length increased. During the reverse transcription reaction, a length of a 3'-terminal priming region may be reduced according to a clamp usage.

Example 7
Effect of a 3' Priming Region of Reverse Transcription Primer Length and Clamp on Reverse Transcription Efficiency A reverse transcription was performed by decreasing a 3'-terminal region length of a reverse transcription primer.

Reaction compositions and conditions for the reverse transcription and PCR are shown in Example 2.

Tables 4 through 8 illustrate the sequences of used templates (miR16, miR21, miR122-5p, and miR200c, respectively), PCR primers, and reverse transcription primers. Clamp C10 (SEQ ID NO: 67) in Example 2 was used as a clamp.

TABLE 4

| | Name | | Sequence |
|---|---|---|---|
| Template | miR16 | | 5'-UAGCAGCACGUAAAUAUUGGCG-3'<br>(SEQ ID NO: 49) |
| PCR primer | Forward primer | | 5'-CGCGCTAGCAGCACGTAAAT-3'<br>(SEQ ID NO: 50) |
| | Reverse primer | | 5'-GTGCAGGGTCCGAGGT-3'<br>(SEQ ID NO: 51) |
| RT primer | V1-RT0 | | 5'-TACGTGCTGCTA GTGCAGGGTCCGAGGT ACTGGATACGAC-3'<br>(SEQ ID NO: 70) |
| | V1-RT1 | | 5'-TACGTGCTGCTA GTGCAGGGTCCGAGGT ACTGGATACGAC C-3'<br>(SEQ ID NO: 71) |
| | V1-RT2 | | 5'-TACGTGCTGCTA GTGCAGGGTCCGAGGT ACTGGATACGAC CG-3'<br>(SEQ ID NO: 72) |
| | V1-RT3 | | 5'-TACGTGCTGCTA GTGCAGGGTCCGAGGT ACTGGATACGAC CGC-3'<br>(SEQ ID NO: 73) |
| | V1-RT4 | | 5'-TACGTGCTGCTA GTGCAGGGTCCGAGGT ACTGGATACGAC CGCC-3'<br>(SEQ ID NO: 74) |
| | V1-RT5 | | 5'-TACGTGCTGCTA GTGCAGGGTCCGAGGT ACTGGATACGAC CGCCA-3'<br>(SEQ ID NO: 75) |
| | V1-RT6 | | 5'-TACGTGCTGCTA GTGCAGGGTCCGAGGT ACTGGATACGAC CGCCAA-3'<br>(SEQ ID NO: 76) |
| | V1-RT7 | | 5'-TACGTGCTGCTA GTGCAGGGTCCGAGGT ACTGGATACGAC CGCCAAT-3'<br>(SEQ ID NO: 77) |
| | V1-RT8 | | 5'-TACGTGCTGCTA GTGCAGGGTCCGAGGT ACTGGATACGAC CGCCAATA-3'<br>(SEQ ID NO: 78) |
| | Linear-RT0 | | 5'-GTGCAGGGTCCGAGGT-3'<br>(SEQ ID NO: 79) |
| | Linear-RT1 | | 5'-GTGCAGGGTCCGAGGT C-3'<br>(SEQ ID NO: 80) |
| | Linear-RT2 | | 5'-GTGCAGGGTCCGAGGT CG-3'<br>(SEQ ID NO: 81) |
| | Linear-RT3 | | 5'-GTGCAGGGTCCGAGGT CGC-3'<br>(SEQ ID NO: 82) |
| | Linear-RT4 | | 5'-GTGCAGGGTCCGAGGT CGCC-3'<br>(SEQ ID NO: 83) |

TABLE 4-continued

| Name | Sequence |
|---|---|
| Linear-RT5 | 5'-GTGCAGGGTCCGAGGT CGCCA-3'<br>(SEQ ID NO: 84) |
| Linear-RT6 | 5'-GTGCAGGGTCCGAGGT CGCCAA-3'<br>(SEQ ID NO: 85) |
| Linear-RT7 | 5'-GTGCAGGGTCCGAGGT CGCCAAT-3'<br>(SEQ ID NO: 86) |
| Linear-RT8 | 5'-GTGCAGGGTCCGAGGT CGCCAATA-3'<br>(SEQ ID NO: 87) |

TABLE 5

| | Name | Sequence |
|---|---|---|
| Template | miR21 | 5'-uagcuuaucagacugauguuga-3'<br>(SEQ ID NO: 88) |
| PCR primer | Forward primer | 5'-cgg tagcttatcagactgatgt-3'<br>(SEQ ID NO: 89) |
| | Reverse primer | 5'-GTGCAGGGTCCGAGGT-3'<br>(SEQ ID NO: 90) |
| RT primer | V1-RT0 | 5'-TCTGATAAGCTA GTGCAGGGTCCGAGGT ACTGGATACGAC-3'<br>(SEQ ID NO: 91) |
| | V1-RT1 | 5'-TCTGATAAGCTA GTGCAGGGTCCGAGGT ACTGGATACGAC T-3'<br>(SEQ ID NO: 92) |
| | V1-RT2 | 5'-TCTGATAAGCTA GTGCAGGGTCCGAGGT ACTGGATACGAC TC-3'<br>(SEQ ID NO: 93) |
| | V1-RT3 | 5'-TCTGATAAGCTA GTGCAGGGTCCGAGGT ACTGGATACGAC TCA-3'<br>(SEQ ID NO: 94) |
| | V1-RT4 | 5'-TCTGATAAGCTA GTGCAGGGTCCGAGGT ACTGGATACGAC TCAA-3'<br>(SEQ ID NO: 95) |
| | V1-RT5 | 5'-TCTGATAAGCTA GTGCAGGGTCCGAGGT ACTGGATACGAC TCAAC-3'<br>(SEQ ID NO: 96) |
| | V1-RT6 | 5'-TCTGATAAGCTA GTGCAGGGTCCGAGGT ACTGGATACGAC TCAACA-3'<br>(SEQ ID NO: 97) |
| | V1-RT7 | 5'-TCTGATAAGCTA GTGCAGGGTCCGAGGT ACTGGATACGAC TCAACAT-3'<br>(SEQ ID NO: 98) |
| | V1-RT8 | 5'-TCTGATAAGCTA GTGCAGGGTCCGAGGT ACTGGATACGAC TCAACATC-3'<br>(SEQ ID NO: 99) |
| | Linear-RT0 | 5'-GTGCAGGGTCCGAGGT-3'<br>(SEQ ID NO: 100) |
| | Linear-RT1 | 5'-GTGCAGGGTCCGAGGT T-3'<br>(SEQ ID NO: 101) |
| | Linear-RT2 | 5'-GTGCAGGGTCCGAGGT TC-3'<br>(SEQ ID NO: 102) |
| | Linear-RT3 | 5'-GTGCAGGGTCCGAGGT TCA-3'<br>(SEQ ID NO: 103) |
| | Linear-RT4 | 5'-GTGCAGGGTCCGAGGT TCAA-3'<br>(SEQ ID NO: 104) |
| | Linear-RT5 | 5'-GTGCAGGGTCCGAGGT TCAAC-3'<br>(SEQ ID NO: 105) |
| | Linear-RT6 | 5'-GTGCAGGGTCCGAGGT TCAACA-3'<br>(SEQ ID NO: 106) |
| | Linear-RT7 | 5'-GTGCAGGGTCCGAGGT TCAACAT-3'<br>(SEQ ID NO: 107) |
| | Linear-RT8 | 5'-GTGCAGGGTCCGAGGT TCAACATC-3'<br>(SEQ ID NO: 108) |

TABLE 6

| | Name | Sequence |
|---|---|---|
| Template | miR210 | 5'-CUGUGCGUGUGACAGCGGCUGA-3'<br>(SEQ ID NO: 109) |
| PCR primer | Forward primer | 5'-CTGTGCGTGTGACAGC-3'<br>(SEQ ID NO: 110) |
| | Reverse primer | 5'-GTGCAGGGTCCGAGGT-3'<br>(SEQ ID NO: 111) |

TABLE 6-continued

| | Name | Sequence |
|---|---|---|
| RT primer | V1-RT0 | 5'-TCACACGCACAG GTGCAGGGTCCGAGGT ACTGGATACGAC-3'<br>(SEQ ID NO: 112) |
| | V1-RT1 | 5'-TCACACGCACAG GTGCAGGGTCCGAGGT ACTGGATACGAC T-3'<br>(SEQ ID NO: 113) |
| | V1-RT2 | 5'-TCACACGCACAG GTGCAGGGTCCGAGGT ACTGGATACGAC TC-3'<br>(SEQ ID NO: 114) |
| | V1-RT3 | 5'-TCACACGCACAG GTGCAGGGTCCGAGGT ACTGGATACGAC TCA-3'<br>(SEQ ID NO: 115) |
| | V1-RT4 | 5'-TCACACGCACAG GTGCAGGGTCCGAGGT ACTGGATACGAC TCAG-3'<br>(SEQ ID NO: 116) |
| | V1-RT5 | 5'-TCACACGCACAG GTGCAGGGTCCGAGGT ACTGGATACGAC TCAGC-3'<br>(SEQ ID NO: 117) |
| | V1-RT6 | 5'-TCACACGCACAG GTGCAGGGTCCGAGGT ACTGGATACGAC TCAGCC-3'<br>(SEQ ID NO: 118) |
| | V1-RT7 | 5'-TCACACGCACAG GTGCAGGGTCCGAGGT ACTGGATACGAC TCAGCCG-3'<br>(SEQ ID NO: 119) |
| | V1-RT8 | 5'-TCACACGCACAG GTGCAGGGTCCGAGGT ACTGGATACGAC TCAGCCGC-3'<br>(SEQ ID NO: 120) |
| | Linear-RT0 | 5'-GTGCAGGGTCCGAGGT-3'<br>(SEQ ID NO: 121) |
| | Linear-RT1 | 5'-GTGCAGGGTCCGAGGT T-3'<br>(SEQ ID NO: 122) |
| | Linear-RT2 | 5'-GTGCAGGGTCCGAGGT TC-3'<br>(SEQ ID NO: 123) |
| | Linear-RT3 | 5'-GTGCAGGGTCCGAGGT TCA-3'<br>(SEQ ID NO: 124) |
| | Linear-RT4 | 5'-GTGCAGGGTCCGAGGT TCAG-3'<br>(SEQ ID NO: 125) |
| | Linear-RT5 | 5'-GTGCAGGGTCCGAGGT TCAGC-3'<br>(SEQ ID NO: 126) |
| | Linear-RT6 | 5'-GTGCAGGGTCCGAGGT TCAGCC-3'<br>(SEQ ID NO: 127) |
| | Linear-RT7 | 5'-GTGCAGGGTCCGAGGT TCAGCCG-3'<br>(SEQ ID NO: 128) |
| | Linear-RT8 | 5'-GTGCAGGGTCCGAGGT TCAGCCGC-3'<br>(SEQ ID NO: 129) |

TABLE 7

| | Name | Sequence |
|---|---|---|
| Template | miR122-5p | 5'-UGGAGUGUGACAAUGGUGUUUG-3'<br>(SEQ ID NO: 130) |
| PCR primer | Forward primer | 5'-CGTGGAGTGTGACAATGG-3'<br>(SEQ ID NO: 131) |
| | Reverse primer | 5'-GTGCAGGGTCCGAGGT-3'<br>(SEQ ID NO: 132) |
| RT primer | V1-RT0 | 5'-TGTCACACTCCA GTGCAGGGTCCGAGGT ACTGGATACGAC-3'<br>(SEQ ID NO: 133) |
| | V1-RT1 | 5'-TGTCACACTCCA GTGCAGGGTCCGAGGT ACTGGATACGAC C-3'<br>(SEQ ID NO: 134) |
| | V1-RT2 | 5'-TGTCACACTCCA GTGCAGGGTCCGAGGT ACTGGATACGAC CA-3'<br>(SEQ ID NO: 135) |
| | V1-RT3 | 5'-TGTCACACTCCA GTGCAGGGTCCGAGGT ACTGGATACGAC CAA-3'<br>(SEQ ID NO: 136) |
| | V1-RT4 | 5'-TGTCACACTCCA GTGCAGGGTCCGAGGT ACTGGATACGAC CAAA-3'<br>(SEQ ID NO: 137) |
| | V1-RT5 | 5'-TGTCACACTCCA GTGCAGGGTCCGAGGT ACTGGATACGAC CAAAC-3'<br>(SEQ ID NO: 138) |
| | V1-RT6 | 5'-TGTCACACTCCA GTGCAGGGTCCGAGGT ACTGGATACGAC CAAACA-3'<br>(SEQ ID NO: 139) |
| | V1-RT7 | 5'-TGTCACACTCCA GTGCAGGGTCCGAGGT ACTGGATACGAC CAAACAC-3'<br>(SEQ ID NO: 140) |
| | V1-RT8 | 5'-TGTCACACTCCA GTGCAGGGTCCGAGGT ACTGGATACGAC CAAACACC-3'<br>(SEQ ID NO: 141) |
| | Linear-RT0 | 5'-GTGCAGGGTCCGAGGT-3'<br>(SEQ ID NO: 142) |
| | Linear-RT1 | 5'-GTGCAGGGTCCGAGGT C-3'<br>(SEQ ID NO: 143) |
| | Linear-RT2 | 5'-GTGCAGGGTCCGAGGT CA-3'<br>(SEQ ID NO: 144) |
| | Linear-RT3 | 5'-GTGCAGGGTCCGAGGT CAA-3'<br>(SEQ ID NO: 145) |

TABLE 7-continued

| Name | Sequence |
|---|---|
| Linear-RT4 | 5'-GTGCAGGGTCCGAGGT CAAA-3' (SEQ ID NO: 146) |
| Linear-RT5 | 5'-GTGCAGGGTCCGAGGT CAAAC-3' (SEQ ID NO: 147) |
| Linear-RT6 | 5'-GTGCAGGGTCCGAGGT CAAACA-3' (SEQ ID NO: 148) |
| Linear-RT7 | 5'-GTGCAGGGTCCGAGGT CAAACAC-3' (SEQ ID NO: 149) |
| Linear-RT8 | 5'-GTGCAGGGTCCGAGGT CAAACACC-3' (SEQ ID NO: 150) |

TABLE 8

| | Name | Sequence |
|---|---|---|
| Template | miR200c | 5'-UAAUACUGCCGGGUAAUGAUGGA-3' (SEQ ID NO: 151) |
| PCR primer | Forward primer | 5'-GGTAATACTGCCGGGTAATGA-3' (SEQ ID NO: 152) |
| | Reverse primer | 5'-GTGCAGGGTCCGAGGT-3' (SEQ ID NO: 153) |
| RT primer | V1-RT0 | 5'-CCGGCAGTATTA GTGCAGGGTCCGAGGT ACTGGATACGAC-3' (SEQ ID NO: 154) |
| | V1-RT1 | 5'-CCGGCAGTATTA GTGCAGGGTCCGAGGT ACTGGATACGAC T-3' (SEQ ID NO: 155) |
| | V1-RT2 | 5'-CCGGCAGTATTA GTGCAGGGTCCGAGGT ACTGGATACGAC TC-3' (SEQ ID NO: 156) |
| | V1-RT3 | 5'-CCGGCAGTATTA GTGCAGGGTCCGAGGT ACTGGATACGAC TCC-3' (SEQ ID NO: 157) |
| | V1-RT4 | 5'-CCGGCAGTATTA GTGCAGGGTCCGAGGT ACTGGATACGAC TCCA-3' (SEQ ID NO: 158) |
| | V1-RT5 | 5'-CCGGCAGTATTA GTGCAGGGTCCGAGGT ACTGGATACGAC TCCAT-3' (SEQ ID NO: 159) |
| | V1-RT6 | 5'-CCGGCAGTATTA GTGCAGGGTCCGAGGT ACTGGATACGAC TCCATC-3' (SEQ ID NO: 160) |
| | V1-RT7 | 5'-CCGGCAGTATTA GTGCAGGGTCCGAGGT ACTGGATACGAC TCCATCA-3' (SEQ ID NO: 161) |
| | V1-RT8 | 5'-CCGGCAGTATTA GTGCAGGGTCCGAGGT ACTGGATACGAC TCCATCAT-3' (SEQ ID NO: 162) |
| | Linear-RT0 | 5'-GTGCAGGGTCCGAGGT-3' (SEQ ID NO: 163) |
| | Linear-RT1 | 5'-GTGCAGGGTCCGAGGT T-3' (SEQ ID NO: 164) |
| | Linear-RT2 | 5'-GTGCAGGGTCCGAGGT TC-3' (SEQ ID NO: 165) |
| | Linear-RT3 | 5'-GTGCAGGGTCCGAGGT TCC-3' (SEQ ID NO: 166) |
| | Linear-RT4 | 5'-GTGCAGGGTCCGAGGT TCCA-3' (SEQ ID NO: 167) |
| | Linear-RT5 | 5'-GTGCAGGGTCCGAGGT TCCAT-3' (SEQ ID NO: 168) |
| | Linear-RT6 | 5'-GTGCAGGGTCCGAGGT TCCATC-3' (SEQ ID NO: 169) |
| | Linear-RT7 | 5'-GTGCAGGGTCCGAGGTTCCATCA-3' (SEQ ID NO: 170) |
| | Linear-RT8 | 5'-GTGCAGGGTCCGAGGTTCCATCAT-3' (SEQ ID NO: 171) |

Figure 10:
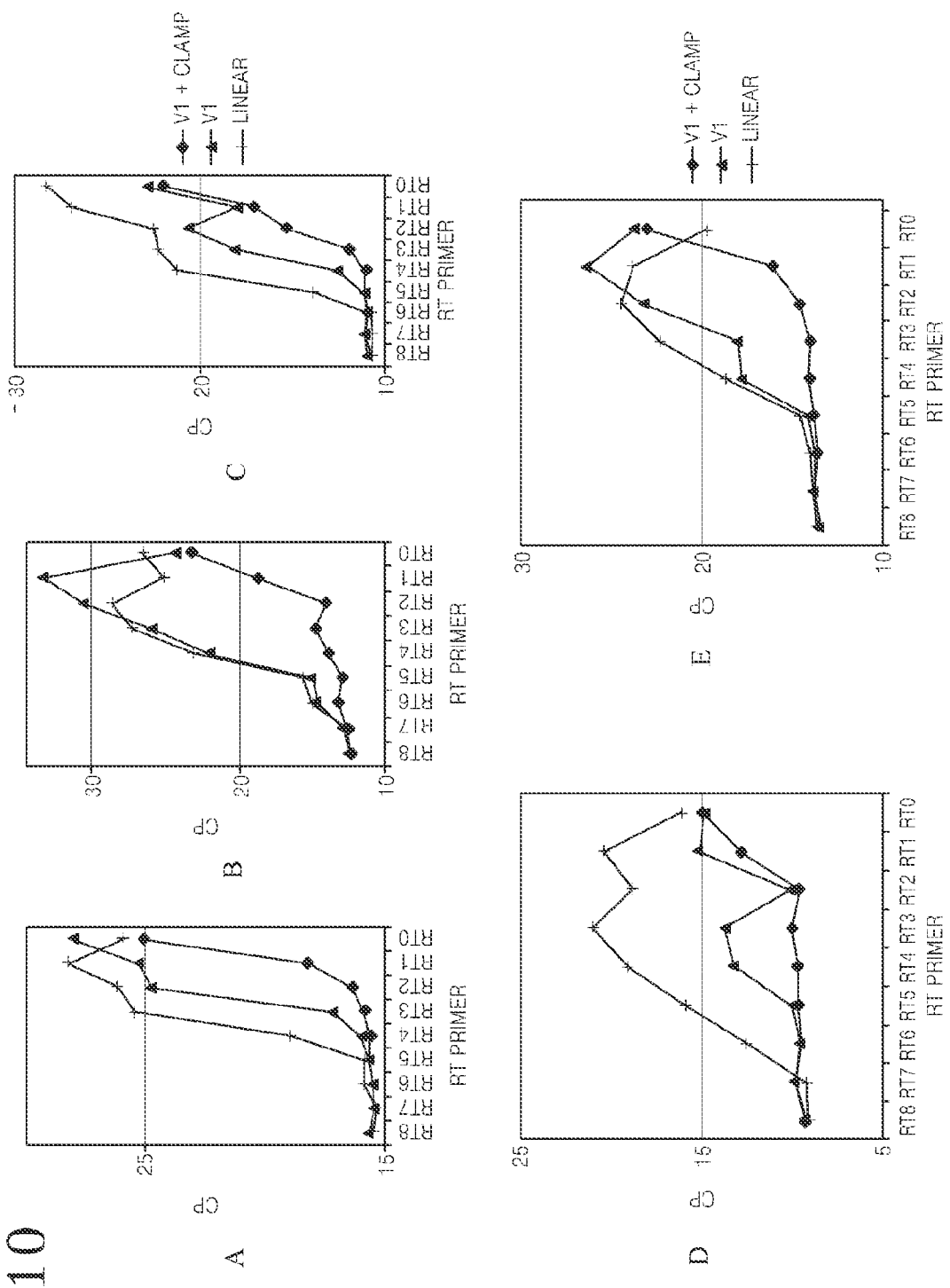
FIGS. 10A through 10E are graphs illustrating the effect of a clamp on the efficiency of a reverse transcription when the target nucleic acid is (A) miR-16, (B) miR-21, (C) miR210, (D) miR-122-5p, and (E) miR-200c.

FIGS. 10A through 10E illustrate an effect of decreasing a 3-terminal priming region length on efficiency of a reverse transcription corresponding to a clamp (FIG. 10A: miR-16, FIG. 10B: miR-21, FIG. 10C: miR-210, FIG. 10D: miR-122-5p, FIG. 10E: miR-200c). As shown in FIGS. 10A through 10E, 3-terminal priming region length may be reduced by using a clamp during the reverse transcription reaction.

As described above, according to the one or more of the above embodiments of the present invention, a polynucleotide may be used to efficiently amplify a target nucleic acid. A composition and kit including the polynucleotide may be used to efficiently amplify the target nucleic acid. A method of producing a nucleotide sequence complementary to the target nucleic acid may be used to efficiently produce the nucleotide sequence complementary to the target nucleic acid.

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A composition for amplifying a target nucleic acid, the composition comprising:
   (a) a target nucleic acid; (b) a first polynucleotide comprising at least two complementary regions that are complementary to the target nucleic acid,
   wherein a first complementary region comprises at least one consecutive nucleotide from the 3'-terminal thereof that is complementary to the 3'-terminal region of the target nucleic acid,
   wherein at least one second complementary region comprises at least one consecutive nucleotide 5' of the first complementary region in the first polynucleotide that is complementary to the 5' terminal region of the target nucleic acid; and
   wherein the first complementary region and the at least one second complementary region are separated by a region of the first polynucleotide that is non-complementary to the target nucleic acid;
   (c) a second polynucleotide consisting of a third complementary region that is complementary to the first polynucleotide in the region that is non-complementary to the target nucleic acid, wherein the 3' terminus of the second polynucleotide is modified.

2. The composition of claim 1, wherein the third complementary region is complementary to at least one consecutive nucleotide of the first polynucleotide that is separated from the first complementary region of the first polynucleotide.

3. The composition of claim 1, wherein the third complementary region is complementary to at least one consecutive nucleotide of the first polynucleotide that is separated from the first complementary region of the first polynucleotide by about 0 to about 20 nucleotides.

4. The composition of claim 1, wherein the 3' terminus of the second polynucleotide comprises of an inverted nucleotide, dideoxynucleotide, an amine group, an alkyl chain moiety, or a combination thereof.

5. A method of producing a nucleotide sequence complementary to a target nucleic acid, the method comprising:
   (a) hybridizing a target nucleic acid with a first polynucleotide comprising at least two complementary regions that are complementary to a target nucleic acid, and a second polynucleotide consisting of a third complementary region complementary to a region of the first polynucleotide, to form a hybridized product,
   wherein a first complementary region of the first polynucleotide comprises at least one consecutive nucleotide from the 3'-terminal thereof that is complementary to the 3' terminal end of the target nucleic acid,
   wherein at least one second complementary region of the first polynucleotide comprises at least one consecutive nucleotide 5' of the first complementary region in the first polynucleotide that is complementary to the 5'-terminal end of the target nucleic acid, and
   wherein the first complementary region and the at least one second complementary region are separated by a region of the first polynucleotide that is non-complementary to the target nucleic acid, and the third complementary region is complementary to the first polynucleotide in the region that is non-complementary to the target nucleic acid, wherein the 3' terminus of the second polynucleotide is modified;

and (b) incubating the hybridized product in the presence of a nucleic acid polymerase to extend a nucleotide sequence complementary to the target nucleic acid from the 3'-terminal of the first polynucleotide.

6. The method of claim 5, wherein the nucleic acid polymerase is a strand displacement nucleic acid polymerase.

7. The method of claim 6, wherein the strand displacement nucleic acid polymerase is at least one reverse transcriptase derived from HIV (Human Immunodeficiency Virus), MMLV (Moloney Murine Leukemia Virus), or AMV (Avian Myeloblastosis Virus).

8. The method of claim 5, wherein the target nucleic acid is RNA.

9. The method of claim 5, wherein the target nucleic acid is microRNA, siRNA, tRNA, non-coding RNA, or a combination thereof.

10. The method of claim 5, wherein hybridizing the first polynucleotide and the target nucleic acid, and hybridizing the first polynucleotide to the second polynucleotide are performed simultaneously or consecutively.

* * * * *

SEQUENCE LISTING

```
<160> NUMBER OF SEQ ID NOS: 182

<210> SEQ ID NO 1
<211> LENGTH: 35
<212> TYPE: DNA
<213> ORGANISM: Artificial Sequence
<220> FEATURE:
<223> OTHER INFORMATION: Synthetic (RCP-3mer)

<400> SEQUENCE: 1
ttacgtgctg ctaggtggta gccttgagga cacgc                                  35

<210> SEQ ID NO 2
<211> LENGTH: 36
<212> TYPE: DNA
<213> ORGANISM: Artificial Sequence
<220> FEATURE:
<223> OTHER INFORMATION: Synthetic (RCP-4mer)

<400> SEQUENCE: 2
ttacgtgctg ctaggtggta gccttgagga cacgcc                                 36

<210> SEQ ID NO 3
<211> LENGTH: 38
<212> TYPE: DNA
<213> ORGANISM: Artificial Sequence
<220> FEATURE:
<223> OTHER INFORMATION: Synthetic (RCP-6mer)

<400> SEQUENCE: 3
ttacgtgctg ctaggtggta gccttgagga cacgccaa                               38

<210> SEQ ID NO 4
<211> LENGTH: 39
<212> TYPE: DNA
<213> ORGANISM: Artificial Sequence
<220> FEATURE:
<223> OTHER INFORMATION: Synthetic (RCP-7mer)

<400> SEQUENCE: 4
ttacgtgctg ctaggtggta gccttgagga cacgccaat                              39
```

```
<210> SEQ ID NO 5
<211> LENGTH: 23
<212> TYPE: DNA
<213> ORGANISM: Artificial Sequence
<220> FEATURE:
<223> OTHER INFORMATION: Synthetic (Linear-3mer)

<400> SEQUENCE: 5
aggtggtagc cttgaggaca cgc                                            23

<210> SEQ ID NO 6
<211> LENGTH: 24
<212> TYPE: DNA
<213> ORGANISM: Artificial Sequence
<220> FEATURE:
<223> OTHER INFORMATION: Synthetic (Linear-4mer)

<400> SEQUENCE: 6
aggtggtagc cttgaggaca cgcc                                           24

<210> SEQ ID NO 7
<211> LENGTH: 26
<212> TYPE: DNA
<213> ORGANISM: Artificial Sequence
<220> FEATURE:
<223> OTHER INFORMATION: Synthetic (Linear-6mer)

<400> SEQUENCE: 7
aggtggtagc cttgaggaca cgccaa                                         26

<210> SEQ ID NO 8
<211> LENGTH: 27
<212> TYPE: DNA
<213> ORGANISM: Artificial Sequence
<220> FEATURE:
<223> OTHER INFORMATION: Synthetic (Linear-7mer)

<400> SEQUENCE: 8
aggtggtagc cttgaggaca cgccaat                                        27

<210> SEQ ID NO 9
<211> LENGTH: 42
<212> TYPE: RNA
<213> ORGANISM: Artificial Sequence
<220> FEATURE:
<223> OTHER INFORMATION: Synthetic (miR-16 RNA with 20nt 5'-tag
      seqeuence)

<400> SEQUENCE: 9
cggugagguc uuugguucau uagcagcacg uaaauauugg cg                       42

<210> SEQ ID NO 10
<211> LENGTH: 20
<212> TYPE: DNA
<213> ORGANISM: Artificial Sequence
<220> FEATURE:
<223> OTHER INFORMATION: Synthetic (Forward PCR primer)

<400> SEQUENCE: 10
cggtgaggtc tttggttcat                                                20

<210> SEQ ID NO 11
<211> LENGTH: 20
<212> TYPE: DNA
<213> ORGANISM: Artificial Sequence
<220> FEATURE:
```

<223> OTHER INFORMATION: Synthetic (Reverse PCR primer)

<400> SEQUENCE: 11
aggtggtagc cttgaggaca          20

<210> SEQ ID NO 12
<211> LENGTH: 38
<212> TYPE: DNA
<213> ORGANISM: Artificial Sequence
<220> FEATURE:
<223> OTHER INFORMATION: Synthetic (RCP RT primer with 6mer 1st
      complementary region)

<400> SEQUENCE: 12
ccacccgccc tcaggtggta gccttgagga catcctcc          38

<210> SEQ ID NO 13
<211> LENGTH: 32
<212> TYPE: DNA
<213> ORGANISM: Artificial Sequence
<220> FEATURE:
<223> OTHER INFORMATION: Synthetic (Control RT primer)

<400> SEQUENCE: 13
aggtggtagc cttgaggaca cgatcgtcct cc          32

<210> SEQ ID NO 14
<211> LENGTH: 39
<212> TYPE: RNA
<213> ORGANISM: Artificial Sequence
<220> FEATURE:
<223> OTHER INFORMATION: Synthetic (miR-3141 with 5'-20nt tag sequence)

<400> SEQUENCE: 14
cggugagguc uuugguucau gagggcgggu ggaggagga          39

<210> SEQ ID NO 15
<211> LENGTH: 28
<212> TYPE: DNA
<213> ORGANISM: Artificial Sequence
<220> FEATURE:
<223> OTHER INFORMATION: Synthetic (RCP with 5' terminal 4mer adaptor
      sequence)

<400> SEQUENCE: 15
cctcaggtgg tagccttgag gacatcct          28

<210> SEQ ID NO 16
<211> LENGTH: 32
<212> TYPE: DNA
<213> ORGANISM: Artificial Sequence
<220> FEATURE:
<223> OTHER INFORMATION: Synthetic (RCP with 5' terminal 8mer adaptor
      sequence)

<400> SEQUENCE: 16
ccgccctcag gtggtagcct tgaggacatc ct          32

<210> SEQ ID NO 17
<211> LENGTH: 34
<212> TYPE: DNA
<213> ORGANISM: Artificial Sequence
<220> FEATURE:
<223> OTHER INFORMATION: Synthetic (RCP with 5' terminal 10mer adaptor
      sequence)

<400> SEQUENCE: 17
acccgccctc aggtggtagc cttgaggaca tcct        34

<210> SEQ ID NO 18
<211> LENGTH: 36
<212> TYPE: DNA
<213> ORGANISM: Artificial Sequence
<220> FEATURE:
<223> OTHER INFORMATION: Synthetic (RCP with 5' terminal 12mer adaptor
      sequence)

<400> SEQUENCE: 18
ccacccgccc tcaggtggta gccttgagga catcct        36

<210> SEQ ID NO 19
<211> LENGTH: 38
<212> TYPE: DNA
<213> ORGANISM: Artificial Sequence
<220> FEATURE:
<223> OTHER INFORMATION: Synthetic (RCP with 5' terminal 14mer adaptor
      sequence)

<400> SEQUENCE: 19
ctccacccgc cctcaggtgg tagccttgag gacatcct        38

<210> SEQ ID NO 20
<211> LENGTH: 39
<212> TYPE: DNA
<213> ORGANISM: Artificial Sequence
<220> FEATURE:
<223> OTHER INFORMATION: Synthetic (RCP with 5' terminal 15mer adaptor
      sequence)

<400> SEQUENCE: 20
cctccacccg ccctcaggtg gtagccttga ggacatcct        39

<210> SEQ ID NO 21
<211> LENGTH: 28
<212> TYPE: DNA
<213> ORGANISM: Artificial Sequence
<220> FEATURE:
<223> OTHER INFORMATION: Synthetic (RCP with 5' terminal 4mer adaptor
      sequence complementary to miR-16)

<400> SEQUENCE: 21
tgctaggtgg tagccttgag gacacgcc        28

<210> SEQ ID NO 22
<211> LENGTH: 32
<212> TYPE: DNA
<213> ORGANISM: Artificial Sequence
<220> FEATURE:
<223> OTHER INFORMATION: Synthetic (RCP with 5' terminal 8mer adaptor
      sequence complementary to miR-16)

<400> SEQUENCE: 22
gtgctgctag gtggtagcct tgaggacacg cc        32

<210> SEQ ID NO 23
<211> LENGTH: 34
<212> TYPE: DNA
<213> ORGANISM: Artificial Sequence
<220> FEATURE:
<223> OTHER INFORMATION: Synthetic (RCP with 5' terminal 10mer adaptor
      sequence complementary to miR-16)

<400> SEQUENCE: 23
acgtgctgct aggtggtagc cttgaggaca cgcc         34

<210> SEQ ID NO 24
<211> LENGTH: 36
<212> TYPE: DNA
<213> ORGANISM: Artificial Sequence
<220> FEATURE:
<223> OTHER INFORMATION: Synthetic (RCP with 5' terminal 12mer adaptor
      sequence complementary to miR-16)

<400> SEQUENCE: 24
ttacgtgctg ctaggtggta gccttgagga cacgcc         36

<210> SEQ ID NO 25
<211> LENGTH: 38
<212> TYPE: DNA
<213> ORGANISM: Artificial Sequence
<220> FEATURE:
<223> OTHER INFORMATION: Synthetic (RCP with 5' terminal 14mer adaptor
      sequence complementary to miR-16)

<400> SEQUENCE: 25
atttacgtgc tgctaggtgg tagccttgag gacacgcc         38

<210> SEQ ID NO 26
<211> LENGTH: 40
<212> TYPE: DNA
<213> ORGANISM: Artificial Sequence
<220> FEATURE:
<223> OTHER INFORMATION: Synthetic (RCP with 5' terminal 16mer adaptor
      sequence complementary to miR-16)

<400> SEQUENCE: 26
atatttacgt gctgctaggt ggtagccttg aggacacgcc         40

<210> SEQ ID NO 27
<211> LENGTH: 36
<212> TYPE: DNA
<213> ORGANISM: Artificial Sequence
<220> FEATURE:
<223> OTHER INFORMATION: Synthetic (RC primer with 6mer 1st
      complementary region)

<400> SEQUENCE: 27
acccgccctc aggtggtagc cttgaggaca tcctcc         36

<210> SEQ ID NO 28
<211> LENGTH: 36
<212> TYPE: DNA
<213> ORGANISM: Artificial Sequence
<220> FEATURE:
<223> OTHER INFORMATION: Synthetic (RC primer with 6mer 1st
      complementary region and M1 mismatch)

<400> SEQUENCE: 28
acccgccctc aggtggtagc cttgaggaca acctcc         36

<210> SEQ ID NO 29
<211> LENGTH: 36
<212> TYPE: DNA
<213> ORGANISM: Artificial Sequence
<220> FEATURE:
<223> OTHER INFORMATION: Synthetic (RC primer with 6mer 1st
      complementary region and M2 mismatch)

<400> SEQUENCE: 29
acccgccctc aggtggtagc cttgaggaca tactcc         36

```
<210> SEQ ID NO 30
<211> LENGTH: 36
<212> TYPE: DNA
<213> ORGANISM: Artificial Sequence
<220> FEATURE:
<223> OTHER INFORMATION: Synthetic (RC primer with 6mer 1st
      complementary region and M3 mismatch)

<400> SEQUENCE: 30
acccgccctc aggtggtagc cttgaggaca tcatcc                              36

<210> SEQ ID NO 31
<211> LENGTH: 36
<212> TYPE: DNA
<213> ORGANISM: Artificial Sequence
<220> FEATURE:
<223> OTHER INFORMATION: Synthetic (RC primer with 6mer 1st
      complementary region and M4 mismatch)

<400> SEQUENCE: 31
acccgccctc aggtggtagc cttgaggaca tccacc                              36

<210> SEQ ID NO 32
<211> LENGTH: 36
<212> TYPE: DNA
<213> ORGANISM: Artificial Sequence
<220> FEATURE:
<223> OTHER INFORMATION: Synthetic (RC primer with 6mer 1st
      complementary region and M5 mismatch)

<400> SEQUENCE: 32
acccgccctc aggtggtagc cttgaggaca tcctac                              36

<210> SEQ ID NO 33
<211> LENGTH: 36
<212> TYPE: DNA
<213> ORGANISM: Artificial Sequence
<220> FEATURE:
<223> OTHER INFORMATION: Synthetic (RC primer with 6mer 1st
      complementary region and M6 mismatch)

<400> SEQUENCE: 33
acccgccctc aggtggtagc cttgaggaca tcctca                              36

<210> SEQ ID NO 34
<211> LENGTH: 34
<212> TYPE: DNA
<213> ORGANISM: Artificial Sequence
<220> FEATURE:
<223> OTHER INFORMATION: Synthetic (RC primer with 4mer 1st
      complementary region)

<400> SEQUENCE: 34
acccgccctc aggtggtagc cttgaggaca tcct                                34

<210> SEQ ID NO 35
<211> LENGTH: 34
<212> TYPE: DNA
<213> ORGANISM: Artificial Sequence
<220> FEATURE:
<223> OTHER INFORMATION: Synthetic (RC primer with 4mer 1st
      complementary region and M1 mismatch)

<400> SEQUENCE: 35
acccgccctc aggtggtagc cttgaggaca acct                                34
```

```
<210> SEQ ID NO 36
<211> LENGTH: 34
<212> TYPE: DNA
<213> ORGANISM: Artificial Sequence
<220> FEATURE:
<223> OTHER INFORMATION: Synthetic (RC primer with 4mer 1st
      complementary region and M2 mismatch)

<400> SEQUENCE: 36
acccgccctc aggtggtagc cttgaggaca tact                             34

<210> SEQ ID NO 37
<211> LENGTH: 34
<212> TYPE: DNA
<213> ORGANISM: Artificial Sequence
<220> FEATURE:
<223> OTHER INFORMATION: Synthetic (RC primer with 4mer 1st
      complementary region and M3 mismatch)

<400> SEQUENCE: 37
acccgccctc aggtggtagc cttgaggaca tcat                             34

<210> SEQ ID NO 38
<211> LENGTH: 34
<212> TYPE: DNA
<213> ORGANISM: Artificial Sequence
<220> FEATURE:
<223> OTHER INFORMATION: Synthetic (RC primer with 4mer 1st
      complementary region and M4 mismatch)

<400> SEQUENCE: 38
acccgccctc aggtggtagc cttgaggaca tcca                             34

<210> SEQ ID NO 39
<211> LENGTH: 33
<212> TYPE: DNA
<213> ORGANISM: Artificial Sequence
<220> FEATURE:
<223> OTHER INFORMATION: Synthetic (RC primer with 3mer 1st
      complementary region)

<400> SEQUENCE: 39
acccgccctc aggtggtagc cttgaggaca tcc                              33

<210> SEQ ID NO 40
<211> LENGTH: 33
<212> TYPE: DNA
<213> ORGANISM: Artificial Sequence
<220> FEATURE:
<223> OTHER INFORMATION: Synthetic (RC primer with 3mer 1st
      complementary region and M1 mismatch)

<400> SEQUENCE: 40
acccgccctc aggtggtagc cttgaggaca acc                              33

<210> SEQ ID NO 41
<211> LENGTH: 33
<212> TYPE: DNA
<213> ORGANISM: Artificial Sequence
<220> FEATURE:
<223> OTHER INFORMATION: Synthetic (RC primer with 3mer 1st
      complementary region and M2 mismatch)

<400> SEQUENCE: 41
acccgccctc aggtggtagc cttgaggaca tac                              33
```

```
<210> SEQ ID NO 42
<211> LENGTH: 33
<212> TYPE: DNA
<213> ORGANISM: Artificial Sequence
<220> FEATURE:
<223> OTHER INFORMATION: Synthetic (RC primer with 3mer 1st
      complementary region and M3 mismatch)

<400> SEQUENCE: 42
acccgccctc aggtggtagc cttgaggaca tca                          33

<210> SEQ ID NO 43
<211> LENGTH: 32
<212> TYPE: DNA
<213> ORGANISM: Artificial Sequence
<220> FEATURE:
<223> OTHER INFORMATION: Synthetic (RC primer with 2mer 1st
      complementary region)

<400> SEQUENCE: 43
acccgccctc aggtggtagc cttgaggaca tc                           32

<210> SEQ ID NO 44
<211> LENGTH: 32
<212> TYPE: DNA
<213> ORGANISM: Artificial Sequence
<220> FEATURE:
<223> OTHER INFORMATION: Synthetic (RC primer with 2mer 1st
      complementary region and M1 mismatch)

<400> SEQUENCE: 44
acccgccctc aggtggtagc cttgaggaca ac                           32

<210> SEQ ID NO 45
<211> LENGTH: 32
<212> TYPE: DNA
<213> ORGANISM: Artificial Sequence
<220> FEATURE:
<223> OTHER INFORMATION: Synthetic (RC primer with 2mer 1st
      complementary region and M2 mismatch)

<400> SEQUENCE: 45
acccgccctc aggtggtagc cttgaggaca aa                           32

<210> SEQ ID NO 46
<211> LENGTH: 31
<212> TYPE: DNA
<213> ORGANISM: Artificial Sequence
<220> FEATURE:
<223> OTHER INFORMATION: Synthetic (RC primer with 1mer 1st
      complementary region)

<400> SEQUENCE: 46
acccgccctc aggtggtagc cttgaggaca t                            31

<210> SEQ ID NO 47
<211> LENGTH: 31
<212> TYPE: DNA
<213> ORGANISM: Artificial Sequence
<220> FEATURE:
<223> OTHER INFORMATION: Synthetic (RC primer with 1mer 1st
      complementary region and M1 mismatch)

<400> SEQUENCE: 47
acccgccctc aggtggtagc cttgaggaca a                            31

<210> SEQ ID NO 48
```

```
<211> LENGTH: 30
<212> TYPE: DNA
<213> ORGANISM: Artificial Sequence
<220> FEATURE:
<223> OTHER INFORMATION: Synthetic (RC primer with 0mer 1st
      complementary region)

<400> SEQUENCE: 48
acccgccctc aggtggtagc cttgaggaca                                    30

<210> SEQ ID NO 49
<211> LENGTH: 22
<212> TYPE: RNA
<213> ORGANISM: Artificial Sequence
<220> FEATURE:
<223> OTHER INFORMATION: Synthetic (miR-16)

<400> SEQUENCE: 49
uagcagcacg uaaauauugg cg                                            22

<210> SEQ ID NO 50
<211> LENGTH: 20
<212> TYPE: DNA
<213> ORGANISM: Artificial Sequence
<220> FEATURE:
<223> OTHER INFORMATION: Synthetic (Forward primer for miR-16)

<400> SEQUENCE: 50
cgcgctagca gcacgtaaat                                               20

<210> SEQ ID NO 51
<211> LENGTH: 16
<212> TYPE: DNA
<213> ORGANISM: Artificial Sequence
<220> FEATURE:
<223> OTHER INFORMATION: Synthetic (Reverse primer for miR-16)

<400> SEQUENCE: 51
gtgcagggtc cgaggt                                                   16

<210> SEQ ID NO 52
<211> LENGTH: 46
<212> TYPE: DNA
<213> ORGANISM: Artificial Sequence
<220> FEATURE:
<223> OTHER INFORMATION: Synthetic (Reverse transcription primer)

<400> SEQUENCE: 52
tacgtgctgc tagtgcaggg tccgaggtat tcgcactgga tacgac                  46

<210> SEQ ID NO 53
<211> LENGTH: 47
<212> TYPE: DNA
<213> ORGANISM: Artificial Sequence
<220> FEATURE:
<223> OTHER INFORMATION: Synthetic (Reverse transcription primer)

<400> SEQUENCE: 53
tacgtgctgc tagtgcaggg tccgaggtat tcgcactgga tacgacc                 47

<210> SEQ ID NO 54
<211> LENGTH: 48
<212> TYPE: DNA
<213> ORGANISM: Artificial Sequence
<220> FEATURE:
<223> OTHER INFORMATION: Synthetic (Reverse transcription primer)
```

-continued

<400> SEQUENCE: 54
tacgtgctgc tagtgcaggg tccgaggtat tcgcactgga tacgaccg    48

<210> SEQ ID NO 55
<211> LENGTH: 49
<212> TYPE: DNA
<213> ORGANISM: Artificial Sequence
<220> FEATURE:
<223> OTHER INFORMATION: Synthetic (Reverse transcription primer)

<400> SEQUENCE: 55
tacgtgctgc tagtgcaggg tccgaggtat tcgcactgga tacgaccgc    49

<210> SEQ ID NO 56
<211> LENGTH: 50
<212> TYPE: DNA
<213> ORGANISM: Artificial Sequence
<220> FEATURE:
<223> OTHER INFORMATION: Synthetic (Reverse transcription primer)

<400> SEQUENCE: 56
tacgtgctgc tagtgcaggg tccgaggtat tcgcactgga tacgaccgcc    50

<210> SEQ ID NO 57
<211> LENGTH: 52
<212> TYPE: DNA
<213> ORGANISM: Artificial Sequence
<220> FEATURE:
<223> OTHER INFORMATION: Synthetic (Reverse transcription primer)

<400> SEQUENCE: 57
tacgtgctgc tagtgcaggg tccgaggtat tcgcactgga tacgaccgcc aa    52

<210> SEQ ID NO 58
<211> LENGTH: 34
<212> TYPE: DNA
<213> ORGANISM: Artificial Sequence
<220> FEATURE:
<223> OTHER INFORMATION: Synthetic (Reverse transcription primer)

<400> SEQUENCE: 58
gtgcagggtc cgaggtattc gcactggata cgac    34

<210> SEQ ID NO 59
<211> LENGTH: 35
<212> TYPE: DNA
<213> ORGANISM: Artificial Sequence
<220> FEATURE:
<223> OTHER INFORMATION: Synthetic (Reverse transcription primer)

<400> SEQUENCE: 59
gtgcagggtc cgaggtattc gcactggata cgacc    35

<210> SEQ ID NO 60
<211> LENGTH: 36
<212> TYPE: DNA
<213> ORGANISM: Artificial Sequence
<220> FEATURE:
<223> OTHER INFORMATION: Synthetic (Reverse transcription primer)

<400> SEQUENCE: 60
gtgcagggtc cgaggtattc gcactggata cgaccg    36

<210> SEQ ID NO 61
<211> LENGTH: 37

```
<212> TYPE: DNA
<213> ORGANISM: Artificial Sequence
<220> FEATURE:
<223> OTHER INFORMATION: Synthetic (Reverse transcription primer)

<400> SEQUENCE: 61
gtgcagggtc cgaggtattc gcactggata cgaccgc                              37

<210> SEQ ID NO 62
<211> LENGTH: 38
<212> TYPE: DNA
<213> ORGANISM: Artificial Sequence
<220> FEATURE:
<223> OTHER INFORMATION: Synthetic (Reverse transcription primer)

<400> SEQUENCE: 62
gtgcagggtc cgaggtattc gcactggata cgaccgcc                             38

<210> SEQ ID NO 63
<211> LENGTH: 40
<212> TYPE: DNA
<213> ORGANISM: Artificial Sequence
<220> FEATURE:
<223> OTHER INFORMATION: Synthetic (Reverse transcription primer)

<400> SEQUENCE: 63
gtgcagggtc cgaggtattc gcactggata cgaccgccaa                           40

<210> SEQ ID NO 64
<211> LENGTH: 16
<212> TYPE: DNA
<213> ORGANISM: Artificial Sequence
<220> FEATURE:
<223> OTHER INFORMATION: Synthetic (Clamp oligonucleotide)

<400> SEQUENCE: 64
gtcgtatcca gtgcga                                                     16

<210> SEQ ID NO 65
<211> LENGTH: 14
<212> TYPE: DNA
<213> ORGANISM: Artificial Sequence
<220> FEATURE:
<223> OTHER INFORMATION: Synthetic (Clamp oligonucleotide)

<400> SEQUENCE: 65
gtcgtatcca gtgc                                                       14

<210> SEQ ID NO 66
<211> LENGTH: 12
<212> TYPE: DNA
<213> ORGANISM: Artificial Sequence
<220> FEATURE:
<223> OTHER INFORMATION: Synthetic (Clamp oligonucleotide)

<400> SEQUENCE: 66
gtcgtatcca gt                                                         12

<210> SEQ ID NO 67
<211> LENGTH: 10
<212> TYPE: DNA
<213> ORGANISM: Artificial Sequence
<220> FEATURE:
<223> OTHER INFORMATION: Synthetic (Clamp oligonucleotide)

<400> SEQUENCE: 67
```

-continued gtcgtatcca                                                              10

<210> SEQ ID NO 68
<211> LENGTH: 8
<212> TYPE: DNA
<213> ORGANISM: Artificial Sequence
<220> FEATURE:
<223> OTHER INFORMATION: Synthetic (Clamp oligonucleotide)

<400> SEQUENCE: 68 gtcgtatc                                                                8

<210> SEQ ID NO 69
<211> LENGTH: 6
<212> TYPE: DNA
<213> ORGANISM: Artificial Sequence
<220> FEATURE:
<223> OTHER INFORMATION: Synthetic (Clamp oligonucleotide)

<400> SEQUENCE: 69 gtcgta                                                                  6

<210> SEQ ID NO 70
<211> LENGTH: 40
<212> TYPE: DNA
<213> ORGANISM: Artificial Sequence
<220> FEATURE:
<223> OTHER INFORMATION: Synthetic (Reverse transcription primer)

<400> SEQUENCE: 70
tacgtgctgc tagtgcaggg tccgaggtac tggatacgac                             40

<210> SEQ ID NO 71
<211> LENGTH: 41
<212> TYPE: DNA
<213> ORGANISM: Artificial Sequence
<220> FEATURE:
<223> OTHER INFORMATION: Synthetic (Reverse transcription primer)

<400> SEQUENCE: 71
tacgtgctgc tagtgcaggg tccgaggtac tggatacgac c                           41

<210> SEQ ID NO 72
<211> LENGTH: 42
<212> TYPE: DNA
<213> ORGANISM: Artificial Sequence
<220> FEATURE:
<223> OTHER INFORMATION: Synthetic (Reverse transcription primer)

<400> SEQUENCE: 72
tacgtgctgc tagtgcaggg tccgaggtac tggatacgac cg                          42

<210> SEQ ID NO 73
<211> LENGTH: 43
<212> TYPE: DNA
<213> ORGANISM: Artificial Sequence
<220> FEATURE:
<223> OTHER INFORMATION: Synthetic (Reverse transcription primer)

<400> SEQUENCE: 73
tacgtgctgc tagtgcaggg tccgaggtac tggatacgac cgc                         43

<210> SEQ ID NO 74
<211> LENGTH: 44
<212> TYPE: DNA
<213> ORGANISM: Artificial Sequence

```
<220> FEATURE:
<223> OTHER INFORMATION: Synthetic (Reverse transcription primer)

<400> SEQUENCE: 74
tacgtgctgc tagtgcaggg tccgaggtac tggatacgac cgcc                    44

<210> SEQ ID NO 75
<211> LENGTH: 45
<212> TYPE: DNA
<213> ORGANISM: Artificial Sequence
<220> FEATURE:
<223> OTHER INFORMATION: Synthetic (Reverse transcription primer)

<400> SEQUENCE: 75
tacgtgctgc tagtgcaggg tccgaggtac tggatacgac cgcca                   45

<210> SEQ ID NO 76
<211> LENGTH: 46
<212> TYPE: DNA
<213> ORGANISM: Artificial Sequence
<220> FEATURE:
<223> OTHER INFORMATION: Synthetic (Reverse transcription primer)

<400> SEQUENCE: 76
tacgtgctgc tagtgcaggg tccgaggtac tggatacgac cgccaa                  46

<210> SEQ ID NO 77
<211> LENGTH: 47
<212> TYPE: DNA
<213> ORGANISM: Artificial Sequence
<220> FEATURE:
<223> OTHER INFORMATION: Synthetic (Reverse transcription primer)

<400> SEQUENCE: 77
tacgtgctgc tagtgcaggg tccgaggtac tggatacgac cgccaat                 47

<210> SEQ ID NO 78
<211> LENGTH: 48
<212> TYPE: DNA
<213> ORGANISM: Artificial Sequence
<220> FEATURE:
<223> OTHER INFORMATION: Synthetic (Reverse transcription primer)

<400> SEQUENCE: 78
tacgtgctgc tagtgcaggg tccgaggtac tggatacgac cgccaata                48

<210> SEQ ID NO 79
<211> LENGTH: 16
<212> TYPE: DNA
<213> ORGANISM: Artificial Sequence
<220> FEATURE:
<223> OTHER INFORMATION: Synthetic (Reverse transcription primer)

<400> SEQUENCE: 79
gtgcagggtc cgaggt                                                   16

<210> SEQ ID NO 80
<211> LENGTH: 17
<212> TYPE: DNA
<213> ORGANISM: Artificial Sequence
<220> FEATURE:
<223> OTHER INFORMATION: Synthetic (Reverse transcription primer)

<400> SEQUENCE: 80
gtgcagggtc cgaggtc                                                  17
```

```
<210> SEQ ID NO 81
<211> LENGTH: 18
<212> TYPE: DNA
<213> ORGANISM: Artificial Sequence
<220> FEATURE:
<223> OTHER INFORMATION: Synthetic (Reverse transcription primer)

<400> SEQUENCE: 81
gtgcagggtc cgaggtcg                                                   18

<210> SEQ ID NO 82
<211> LENGTH: 19
<212> TYPE: DNA
<213> ORGANISM: Artificial Sequence
<220> FEATURE:
<223> OTHER INFORMATION: Synthetic (Reverse transcription primer)

<400> SEQUENCE: 82
gtgcagggtc cgaggtcgc                                                  19

<210> SEQ ID NO 83
<211> LENGTH: 20
<212> TYPE: DNA
<213> ORGANISM: Artificial Sequence
<220> FEATURE:
<223> OTHER INFORMATION: Synthetic (Reverse transcription primer)

<400> SEQUENCE: 83
gtgcagggtc cgaggtcgcc                                                 20

<210> SEQ ID NO 84
<211> LENGTH: 21
<212> TYPE: DNA
<213> ORGANISM: Artificial Sequence
<220> FEATURE:
<223> OTHER INFORMATION: Synthetic (Reverse transcription primer)

<400> SEQUENCE: 84
gtgcagggtc cgaggtcgcc a                                               21

<210> SEQ ID NO 85
<211> LENGTH: 22
<212> TYPE: DNA
<213> ORGANISM: Artificial Sequence
<220> FEATURE:
<223> OTHER INFORMATION: Synthetic (Reverse transcription primer)

<400> SEQUENCE: 85
gtgcagggtc cgaggtcgcc aa                                              22

<210> SEQ ID NO 86
<211> LENGTH: 23
<212> TYPE: DNA
<213> ORGANISM: Artificial Sequence
<220> FEATURE:
<223> OTHER INFORMATION: Synthetic (Reverse transcription primer)

<400> SEQUENCE: 86
gtgcagggtc cgaggtcgcc aat                                             23

<210> SEQ ID NO 87
<211> LENGTH: 24
<212> TYPE: DNA
<213> ORGANISM: Artificial Sequence
<220> FEATURE:
<223> OTHER INFORMATION: Synthetic (Reverse transcription primer)
```

<400> SEQUENCE: 87
gtgcagggtc cgaggtcgcc aata                                    24

<210> SEQ ID NO 88
<211> LENGTH: 22
<212> TYPE: RNA
<213> ORGANISM: Artificial Sequence
<220> FEATURE:
<223> OTHER INFORMATION: Synthetic (miR-21)

<400> SEQUENCE: 88
uagcuuauca gacugauguu ga                                      22

<210> SEQ ID NO 89
<211> LENGTH: 22
<212> TYPE: DNA
<213> ORGANISM: Artificial Sequence
<220> FEATURE:
<223> OTHER INFORMATION: Synthetic (Forward primer for miR-21)

<400> SEQUENCE: 89
cggtagctta tcagactgat gt                                      22

<210> SEQ ID NO 90
<211> LENGTH: 16
<212> TYPE: DNA
<213> ORGANISM: Artificial Sequence
<220> FEATURE:
<223> OTHER INFORMATION: Synthetic (Reverse primer for miR-21)

<400> SEQUENCE: 90
gtgcagggtc cgaggt                                             16

<210> SEQ ID NO 91
<211> LENGTH: 40
<212> TYPE: DNA
<213> ORGANISM: Artificial Sequence
<220> FEATURE:
<223> OTHER INFORMATION: Synthetic (Reverse transcription primer)

<400> SEQUENCE: 91
tctgataagc tagtgcaggg tccgaggtac tggatacgac                   40

<210> SEQ ID NO 92
<211> LENGTH: 41
<212> TYPE: DNA
<213> ORGANISM: Artificial Sequence
<220> FEATURE:
<223> OTHER INFORMATION: Synthetic (Reverse transcription primer)

<400> SEQUENCE: 92
tctgataagc tagtgcaggg tccgaggtac tggatacgac t                 41

<210> SEQ ID NO 93
<211> LENGTH: 42
<212> TYPE: DNA
<213> ORGANISM: Artificial Sequence
<220> FEATURE:
<223> OTHER INFORMATION: Synthetic (Reverse transcription primer)

<400> SEQUENCE: 93
tctgataagc tagtgcaggg tccgaggtac tggatacgac tc                42

<210> SEQ ID NO 94

```
<211> LENGTH: 43
<212> TYPE: DNA
<213> ORGANISM: Artificial Sequence
<220> FEATURE:
<223> OTHER INFORMATION: Synthetic (Reverse transcription primer)

<400> SEQUENCE: 94
tctgataagc tagtgcaggg tccgaggtac tggatacgac tca                    43

<210> SEQ ID NO 95
<211> LENGTH: 44
<212> TYPE: DNA
<213> ORGANISM: Artificial Sequence
<220> FEATURE:
<223> OTHER INFORMATION: Synthetic (Reverse transcription primer)

<400> SEQUENCE: 95
tctgataagc tagtgcaggg tccgaggtac tggatacgac tcaa                   44

<210> SEQ ID NO 96
<211> LENGTH: 45
<212> TYPE: DNA
<213> ORGANISM: Artificial Sequence
<220> FEATURE:
<223> OTHER INFORMATION: Synthetic (Reverse transcription primer)

<400> SEQUENCE: 96
tctgataagc tagtgcaggg tccgaggtac tggatacgac tcaac                  45

<210> SEQ ID NO 97
<211> LENGTH: 46
<212> TYPE: DNA
<213> ORGANISM: Artificial Sequence
<220> FEATURE:
<223> OTHER INFORMATION: Synthetic (Reverse transcription primer)

<400> SEQUENCE: 97
tctgataagc tagtgcaggg tccgaggtac tggatacgac tcaaca                 46

<210> SEQ ID NO 98
<211> LENGTH: 47
<212> TYPE: DNA
<213> ORGANISM: Artificial Sequence
<220> FEATURE:
<223> OTHER INFORMATION: Synthetic (Reverse transcription primer)

<400> SEQUENCE: 98
tctgataagc tagtgcaggg tccgaggtac tggatacgac tcaacat                47

<210> SEQ ID NO 99
<211> LENGTH: 48
<212> TYPE: DNA
<213> ORGANISM: Artificial Sequence
<220> FEATURE:
<223> OTHER INFORMATION: Synthetic (Reverse transcription primer)

<400> SEQUENCE: 99
tctgataagc tagtgcaggg tccgaggtac tggatacgac tcaacatc               48

<210> SEQ ID NO 100
<211> LENGTH: 16
<212> TYPE: DNA
<213> ORGANISM: Artificial Sequence
<220> FEATURE:
<223> OTHER INFORMATION: Synthetic (Reverse transcription primer)

<400> SEQUENCE: 100
```

| | | |
|---|---|---|
| gtgcagggtc cgaggt | | 16 |

<210> SEQ ID NO 101
<211> LENGTH: 17
<212> TYPE: DNA
<213> ORGANISM: Artificial Sequence
<220> FEATURE:
<223> OTHER INFORMATION: Synthetic (Reverse transcription primer)

<400> SEQUENCE: 101

| | | |
|---|---|---|
| gtgcagggtc cgaggtt | | 17 |

<210> SEQ ID NO 102
<211> LENGTH: 18
<212> TYPE: DNA
<213> ORGANISM: Artificial Sequence
<220> FEATURE:
<223> OTHER INFORMATION: Synthetic (Reverse transcription primer)

<400> SEQUENCE: 102

| | | |
|---|---|---|
| gtgcagggtc cgaggttc | | 18 |

<210> SEQ ID NO 103
<211> LENGTH: 19
<212> TYPE: DNA
<213> ORGANISM: Artificial Sequence
<220> FEATURE:
<223> OTHER INFORMATION: Synthetic (Reverse transcription primer)

<400> SEQUENCE: 103

| | | |
|---|---|---|
| gtgcagggtc cgaggttca | | 19 |

<210> SEQ ID NO 104
<211> LENGTH: 20
<212> TYPE: DNA
<213> ORGANISM: Artificial Sequence
<220> FEATURE:
<223> OTHER INFORMATION: Synthetic (Reverse transcription primer)

<400> SEQUENCE: 104

| | | |
|---|---|---|
| gtgcagggtc cgaggttcaa | | 20 |

<210> SEQ ID NO 105
<211> LENGTH: 21
<212> TYPE: DNA
<213> ORGANISM: Artificial Sequence
<220> FEATURE:
<223> OTHER INFORMATION: Synthetic (Reverse transcription primer)

<400> SEQUENCE: 105

| | | |
|---|---|---|
| gtgcagggtc cgaggttcaa c | | 21 |

<210> SEQ ID NO 106
<211> LENGTH: 22
<212> TYPE: DNA
<213> ORGANISM: Artificial Sequence
<220> FEATURE:
<223> OTHER INFORMATION: Synthetic (Reverse transcription primer)

<400> SEQUENCE: 106

| | | |
|---|---|---|
| gtgcagggtc cgaggttcaa ca | | 22 |

<210> SEQ ID NO 107
<211> LENGTH: 23
<212> TYPE: DNA

<213> ORGANISM: Artificial Sequence
<220> FEATURE:
<223> OTHER INFORMATION: Synthetic (Reverse transcription primer)

<400> SEQUENCE: 107
gtgcagggtc cgaggttcaa cat                                    23

<210> SEQ ID NO 108
<211> LENGTH: 24
<212> TYPE: DNA
<213> ORGANISM: Artificial Sequence
<220> FEATURE:
<223> OTHER INFORMATION: Synthetic (Reverse transcription primer)

<400> SEQUENCE: 108
gtgcagggtc cgaggttcaa catc                                   24

<210> SEQ ID NO 109
<211> LENGTH: 22
<212> TYPE: RNA
<213> ORGANISM: Artificial Sequence
<220> FEATURE:
<223> OTHER INFORMATION: Synthetic (miR-210)

<400> SEQUENCE: 109
cugugcgugu gacagcggcu ga                                     22

<210> SEQ ID NO 110
<211> LENGTH: 16
<212> TYPE: DNA
<213> ORGANISM: Artificial Sequence
<220> FEATURE:
<223> OTHER INFORMATION: Synthetic (Forward primer for miR-210)

<400> SEQUENCE: 110
ctgtgcgtgt gacagc                                            16

<210> SEQ ID NO 111
<211> LENGTH: 16
<212> TYPE: DNA
<213> ORGANISM: Artificial Sequence
<220> FEATURE:
<223> OTHER INFORMATION: Synthetic (Reverse primer for miR-210)

<400> SEQUENCE: 111
gtgcagggtc cgaggt                                            16

<210> SEQ ID NO 112
<211> LENGTH: 40
<212> TYPE: DNA
<213> ORGANISM: Artificial Sequence
<220> FEATURE:
<223> OTHER INFORMATION: Synthetic (Reverse transcription primer)

<400> SEQUENCE: 112
tcacacgcac aggtgcaggg tccgaggtac tggatacgac                  40

<210> SEQ ID NO 113
<211> LENGTH: 41
<212> TYPE: DNA
<213> ORGANISM: Artificial Sequence
<220> FEATURE:
<223> OTHER INFORMATION: Synthetic (Reverse transcription primer)

<400> SEQUENCE: 113
tcacacgcac aggtgcaggg tccgaggtac tggatacgac t                41

<210> SEQ ID NO 114
<211> LENGTH: 42
<212> TYPE: DNA
<213> ORGANISM: Artificial Sequence
<220> FEATURE:
<223> OTHER INFORMATION: Synthetic (Reverse transcription primer)

<400> SEQUENCE: 114
tcacacgcac aggtgcaggg tccgaggtac tggatacgac tc          42

<210> SEQ ID NO 115
<211> LENGTH: 43
<212> TYPE: DNA
<213> ORGANISM: Artificial Sequence
<220> FEATURE:
<223> OTHER INFORMATION: Synthetic (Reverse transcription primer)

<400> SEQUENCE: 115
tcacacgcac aggtgcaggg tccgaggtac tggatacgac tca         43

<210> SEQ ID NO 116
<211> LENGTH: 44
<212> TYPE: DNA
<213> ORGANISM: Artificial Sequence
<220> FEATURE:
<223> OTHER INFORMATION: Synthetic (Reverse transcription primer)

<400> SEQUENCE: 116
tcacacgcac aggtgcaggg tccgaggtac tggatacgac tcag        44

<210> SEQ ID NO 117
<211> LENGTH: 45
<212> TYPE: DNA
<213> ORGANISM: Artificial Sequence
<220> FEATURE:
<223> OTHER INFORMATION: Synthetic (Reverse transcription primer)

<400> SEQUENCE: 117
tcacacgcac aggtgcaggg tccgaggtac tggatacgac tcagc       45

<210> SEQ ID NO 118
<211> LENGTH: 46
<212> TYPE: DNA
<213> ORGANISM: Artificial Sequence
<220> FEATURE:
<223> OTHER INFORMATION: Synthetic (Reverse transcription primer)

<400> SEQUENCE: 118
tcacacgcac aggtgcaggg tccgaggtac tggatacgac tcagcc      46

<210> SEQ ID NO 119
<211> LENGTH: 47
<212> TYPE: DNA
<213> ORGANISM: Artificial Sequence
<220> FEATURE:
<223> OTHER INFORMATION: Synthetic (Reverse transcription primer)

<400> SEQUENCE: 119
tcacacgcac aggtgcaggg tccgaggtac tggatacgac tcagccg     47

<210> SEQ ID NO 120
<211> LENGTH: 48
<212> TYPE: DNA
<213> ORGANISM: Artificial Sequence
<220> FEATURE:

<223> OTHER INFORMATION: Synthetic (Reverse transcription primer)

<400> SEQUENCE: 120
tcacacgcac aggtgcaggg tccgaggtac tggatacgac tcagccgc         48

<210> SEQ ID NO 121
<211> LENGTH: 16
<212> TYPE: DNA
<213> ORGANISM: Artificial Sequence
<220> FEATURE:
<223> OTHER INFORMATION: Synthetic (Reverse transcription primer)

<400> SEQUENCE: 121
gtgcagggtc cgaggt         16

<210> SEQ ID NO 122
<211> LENGTH: 17
<212> TYPE: DNA
<213> ORGANISM: Artificial Sequence
<220> FEATURE:
<223> OTHER INFORMATION: Synthetic (Reverse transcription primer)

<400> SEQUENCE: 122
gtgcagggtc cgaggtt         17

<210> SEQ ID NO 123
<211> LENGTH: 18
<212> TYPE: DNA
<213> ORGANISM: Artificial Sequence
<220> FEATURE:
<223> OTHER INFORMATION: Synthetic (Reverse transcription primer)

<400> SEQUENCE: 123
gtgcagggtc cgaggttc         18

<210> SEQ ID NO 124
<211> LENGTH: 19
<212> TYPE: DNA
<213> ORGANISM: Artificial Sequence
<220> FEATURE:
<223> OTHER INFORMATION: Synthetic (Reverse transcription primer)

<400> SEQUENCE: 124
gtgcagggtc cgaggttca         19

<210> SEQ ID NO 125
<211> LENGTH: 20
<212> TYPE: DNA
<213> ORGANISM: Artificial Sequence
<220> FEATURE:
<223> OTHER INFORMATION: Synthetic (Reverse transcription primer)

<400> SEQUENCE: 125
gtgcagggtc cgaggttcag         20

<210> SEQ ID NO 126
<211> LENGTH: 21
<212> TYPE: DNA
<213> ORGANISM: Artificial Sequence
<220> FEATURE:
<223> OTHER INFORMATION: Synthetic (Reverse transcription primer)

<400> SEQUENCE: 126
gtgcagggtc cgaggttcag c         21

```
<210> SEQ ID NO 127
<211> LENGTH: 22
<212> TYPE: DNA
<213> ORGANISM: Artificial Sequence
<220> FEATURE:
<223> OTHER INFORMATION: Synthetic (Reverse transcription primer)

<400> SEQUENCE: 127
gtgcagggtc cgaggttcag cc                                              22

<210> SEQ ID NO 128
<211> LENGTH: 23
<212> TYPE: DNA
<213> ORGANISM: Artificial Sequence
<220> FEATURE:
<223> OTHER INFORMATION: Synthetic (Reverse transcription primer)

<400> SEQUENCE: 128
gtgcagggtc cgaggttcag ccg                                             23

<210> SEQ ID NO 129
<211> LENGTH: 24
<212> TYPE: DNA
<213> ORGANISM: Artificial Sequence
<220> FEATURE:
<223> OTHER INFORMATION: Synthetic (Reverse transcription primer)

<400> SEQUENCE: 129
gtgcagggtc cgaggttcag ccgc                                            24

<210> SEQ ID NO 130
<211> LENGTH: 22
<212> TYPE: RNA
<213> ORGANISM: Artificial Sequence
<220> FEATURE:
<223> OTHER INFORMATION: Synthetic (miR-122-5p)

<400> SEQUENCE: 130
uggaguguga caaugguguu ug                                              22

<210> SEQ ID NO 131
<211> LENGTH: 18
<212> TYPE: DNA
<213> ORGANISM: Artificial Sequence
<220> FEATURE:
<223> OTHER INFORMATION: Synthetic (Forward primer for miR-122-5p)

<400> SEQUENCE: 131
cgtggagtgt gacaatgg                                                   18

<210> SEQ ID NO 132
<211> LENGTH: 16
<212> TYPE: DNA
<213> ORGANISM: Artificial Sequence
<220> FEATURE:
<223> OTHER INFORMATION: Synthetic (Reverse primer for miR-122-5p)

<400> SEQUENCE: 132
gtgcagggtc cgaggt                                                     16

<210> SEQ ID NO 133
<211> LENGTH: 40
<212> TYPE: DNA
<213> ORGANISM: Artificial Sequence
<220> FEATURE:
<223> OTHER INFORMATION: Synthetic (Reverse transcription primer)
```

```
<400> SEQUENCE: 133
tgtcacactc cagtgcaggg tccgaggtac tggatacgac                                40

<210> SEQ ID NO 134
<211> LENGTH: 41
<212> TYPE: DNA
<213> ORGANISM: Artificial Sequence
<220> FEATURE:
<223> OTHER INFORMATION: Synthetic (Reverse transcription primer)

<400> SEQUENCE: 134
tgtcacactc cagtgcaggg tccgaggtac tggatacgac c                              41

<210> SEQ ID NO 135
<211> LENGTH: 42
<212> TYPE: DNA
<213> ORGANISM: Artificial Sequence
<220> FEATURE:
<223> OTHER INFORMATION: Synthetic (Reverse transcription primer)

<400> SEQUENCE: 135
tgtcacactc cagtgcaggg tccgaggtac tggatacgac ca                             42

<210> SEQ ID NO 136
<211> LENGTH: 43
<212> TYPE: DNA
<213> ORGANISM: Artificial Sequence
<220> FEATURE:
<223> OTHER INFORMATION: Synthetic (Reverse transcription primer)

<400> SEQUENCE: 136
tgtcacactc cagtgcaggg tccgaggtac tggatacgac caa                            43

<210> SEQ ID NO 137
<211> LENGTH: 44
<212> TYPE: DNA
<213> ORGANISM: Artificial Sequence
<220> FEATURE:
<223> OTHER INFORMATION: Synthetic (Reverse transcription primer)

<400> SEQUENCE: 137
tgtcacactc cagtgcaggg tccgaggtac tggatacgac caaa                           44

<210> SEQ ID NO 138
<211> LENGTH: 45
<212> TYPE: DNA
<213> ORGANISM: Artificial Sequence
<220> FEATURE:
<223> OTHER INFORMATION: Synthetic (Reverse transcription primer)

<400> SEQUENCE: 138
tgtcacactc cagtgcaggg tccgaggtac tggatacgac caaac                          45

<210> SEQ ID NO 139
<211> LENGTH: 46
<212> TYPE: DNA
<213> ORGANISM: Artificial Sequence
<220> FEATURE:
<223> OTHER INFORMATION: Synthetic (Reverse transcription primer)

<400> SEQUENCE: 139
tgtcacactc cagtgcaggg tccgaggtac tggatacgac caaaca                         46

<210> SEQ ID NO 140
<211> LENGTH: 47
```

```
<212> TYPE: DNA
<213> ORGANISM: Artificial Sequence
<220> FEATURE:
<223> OTHER INFORMATION: Synthetic (Reverse transcription primer)

<400> SEQUENCE: 140
tgtcacactc cagtgcaggg tccgaggtac tggatacgac caaacac        47

<210> SEQ ID NO 141
<211> LENGTH: 48
<212> TYPE: DNA
<213> ORGANISM: Artificial Sequence
<220> FEATURE:
<223> OTHER INFORMATION: Synthetic (Reverse transcription primer)

<400> SEQUENCE: 141
tgtcacactc cagtgcaggg tccgaggtac tggatacgac caaacacc       48

<210> SEQ ID NO 142
<211> LENGTH: 16
<212> TYPE: DNA
<213> ORGANISM: Artificial Sequence
<220> FEATURE:
<223> OTHER INFORMATION: Synthetic (Reverse transcription primer)

<400> SEQUENCE: 142
gtgcagggtc cgaggt                                           16

<210> SEQ ID NO 143
<211> LENGTH: 17
<212> TYPE: DNA
<213> ORGANISM: Artificial Sequence
<220> FEATURE:
<223> OTHER INFORMATION: Synthetic (Reverse transcription primer)

<400> SEQUENCE: 143
gtgcagggtc cgaggtc                                          17

<210> SEQ ID NO 144
<211> LENGTH: 18
<212> TYPE: DNA
<213> ORGANISM: Artificial Sequence
<220> FEATURE:
<223> OTHER INFORMATION: Synthetic (Reverse transcription primer)

<400> SEQUENCE: 144
gtgcagggtc cgaggtca                                         18

<210> SEQ ID NO 145
<211> LENGTH: 19
<212> TYPE: DNA
<213> ORGANISM: Artificial Sequence
<220> FEATURE:
<223> OTHER INFORMATION: Synthetic (Reverse transcription primer)

<400> SEQUENCE: 145
gtgcagggtc cgaggtcaa                                        19

<210> SEQ ID NO 146
<211> LENGTH: 20
<212> TYPE: DNA
<213> ORGANISM: Artificial Sequence
<220> FEATURE:
<223> OTHER INFORMATION: Synthetic (Reverse transcription primer)

<400> SEQUENCE: 146
```
gtgcagggtc cgaggtcaaa                                                   20

<210> SEQ ID NO 147
<211> LENGTH: 21
<212> TYPE: DNA
<213> ORGANISM: Artificial Sequence
<220> FEATURE:
<223> OTHER INFORMATION: Synthetic (Reverse transcription primer)

<400> SEQUENCE: 147
gtgcagggtc cgaggtcaaa c                                                 21

<210> SEQ ID NO 148
<211> LENGTH: 22
<212> TYPE: DNA
<213> ORGANISM: Artificial Sequence
<220> FEATURE:
<223> OTHER INFORMATION: Synthetic (Reverse transcription primer)

<400> SEQUENCE: 148
gtgcagggtc cgaggtcaaa ca                                                22

<210> SEQ ID NO 149
<211> LENGTH: 23
<212> TYPE: DNA
<213> ORGANISM: Artificial Sequence
<220> FEATURE:
<223> OTHER INFORMATION: Synthetic (Reverse transcription primer)

<400> SEQUENCE: 149
gtgcagggtc cgaggtcaaa cac                                               23

<210> SEQ ID NO 150
<211> LENGTH: 24
<212> TYPE: DNA
<213> ORGANISM: Artificial Sequence
<220> FEATURE:
<223> OTHER INFORMATION: Synthetic (Reverse transcription primer)

<400> SEQUENCE: 150
gtgcagggtc cgaggtcaaa cacc                                              24

<210> SEQ ID NO 151
<211> LENGTH: 23
<212> TYPE: RNA
<213> ORGANISM: Artificial Sequence
<220> FEATURE:
<223> OTHER INFORMATION: Synthetic (miR-200c)

<400> SEQUENCE: 151
uaauacugcc ggguaaugau gga                                               23

<210> SEQ ID NO 152
<211> LENGTH: 21
<212> TYPE: DNA
<213> ORGANISM: Artificial Sequence
<220> FEATURE:
<223> OTHER INFORMATION: Synthetic (Forward primer for miR-200c)

<400> SEQUENCE: 152
ggtaatactg ccgggtaatg a                                                 21

<210> SEQ ID NO 153
<211> LENGTH: 16
<212> TYPE: DNA
<213> ORGANISM: Artificial Sequence

```
<220> FEATURE:
<223> OTHER INFORMATION: Synthetic (Reverse primer for miR-200c)

<400> SEQUENCE: 153
gtgcagggtc cgaggt                                                    16

<210> SEQ ID NO 154
<211> LENGTH: 40
<212> TYPE: DNA
<213> ORGANISM: Artificial Sequence
<220> FEATURE:
<223> OTHER INFORMATION: Synthetic (Reverse transcription primer)

<400> SEQUENCE: 154
ccggcagtat tagtgcaggg tccgaggtac tggatacgac                          40

<210> SEQ ID NO 155
<211> LENGTH: 41
<212> TYPE: DNA
<213> ORGANISM: Artificial Sequence
<220> FEATURE:
<223> OTHER INFORMATION: Synthetic (Reverse transcription primer)

<400> SEQUENCE: 155
ccggcagtat tagtgcaggg tccgaggtac tggatacgac t                        41

<210> SEQ ID NO 156
<211> LENGTH: 42
<212> TYPE: DNA
<213> ORGANISM: Artificial Sequence
<220> FEATURE:
<223> OTHER INFORMATION: Synthetic (Reverse transcription primer)

<400> SEQUENCE: 156
ccggcagtat tagtgcaggg tccgaggtac tggatacgac tc                       42

<210> SEQ ID NO 157
<211> LENGTH: 43
<212> TYPE: DNA
<213> ORGANISM: Artificial Sequence
<220> FEATURE:
<223> OTHER INFORMATION: Synthetic (Reverse transcription primer)

<400> SEQUENCE: 157
ccggcagtat tagtgcaggg tccgaggtac tggatacgac tcc                      43

<210> SEQ ID NO 158
<211> LENGTH: 44
<212> TYPE: DNA
<213> ORGANISM: Artificial Sequence
<220> FEATURE:
<223> OTHER INFORMATION: Synthetic (Reverse transcription primer)

<400> SEQUENCE: 158
ccggcagtat tagtgcaggg tccgaggtac tggatacgac tcca                     44

<210> SEQ ID NO 159
<211> LENGTH: 45
<212> TYPE: DNA
<213> ORGANISM: Artificial Sequence
<220> FEATURE:
<223> OTHER INFORMATION: Synthetic (Reverse transcription primer)

<400> SEQUENCE: 159
ccggcagtat tagtgcaggg tccgaggtac tggatacgac tccat                    45
```

<210> SEQ ID NO 160
<211> LENGTH: 46
<212> TYPE: DNA
<213> ORGANISM: Artificial Sequence
<220> FEATURE:
<223> OTHER INFORMATION: Synthetic (Reverse transcription primer)

<400> SEQUENCE: 160
ccggcagtat tagtgcaggg tccgaggtac tggatacgac tccatc    46

<210> SEQ ID NO 161
<211> LENGTH: 47
<212> TYPE: DNA
<213> ORGANISM: Artificial Sequence
<220> FEATURE:
<223> OTHER INFORMATION: Synthetic (Reverse transcription primer)

<400> SEQUENCE: 161
ccggcagtat tagtgcaggg tccgaggtac tggatacgac tccatca    47

<210> SEQ ID NO 162
<211> LENGTH: 48
<212> TYPE: DNA
<213> ORGANISM: Artificial Sequence
<220> FEATURE:
<223> OTHER INFORMATION: Synthetic (Reverse transcription primer)

<400> SEQUENCE: 162
ccggcagtat tagtgcaggg tccgaggtac tggatacgac tccatcat    48

<210> SEQ ID NO 163
<211> LENGTH: 16
<212> TYPE: DNA
<213> ORGANISM: Artificial Sequence
<220> FEATURE:
<223> OTHER INFORMATION: Synthetic (Reverse transcription primer)

<400> SEQUENCE: 163
gtgcagggtc cgaggt    16

<210> SEQ ID NO 164
<211> LENGTH: 17
<212> TYPE: DNA
<213> ORGANISM: Artificial Sequence
<220> FEATURE:
<223> OTHER INFORMATION: Synthetic (Reverse transcription primer)

<400> SEQUENCE: 164
gtgcagggtc cgaggtt    17

<210> SEQ ID NO 165
<211> LENGTH: 18
<212> TYPE: DNA
<213> ORGANISM: Artificial Sequence
<220> FEATURE:
<223> OTHER INFORMATION: Synthetic (Reverse transcription primer)

<400> SEQUENCE: 165
gtgcagggtc cgaggttc    18

<210> SEQ ID NO 166
<211> LENGTH: 19
<212> TYPE: DNA
<213> ORGANISM: Artificial Sequence
<220> FEATURE:
<223> OTHER INFORMATION: Synthetic (Reverse transcription primer)

```
<400> SEQUENCE: 166
gtgcagggtc cgaggttcc                                                    19

<210> SEQ ID NO 167
<211> LENGTH: 20
<212> TYPE: DNA
<213> ORGANISM: Artificial Sequence
<220> FEATURE:
<223> OTHER INFORMATION: Synthetic (Reverse transcription primer)

<400> SEQUENCE: 167
gtgcagggtc cgaggttcca                                                   20

<210> SEQ ID NO 168
<211> LENGTH: 21
<212> TYPE: DNA
<213> ORGANISM: Artificial Sequence
<220> FEATURE:
<223> OTHER INFORMATION: Synthetic (Reverse transcription primer)

<400> SEQUENCE: 168
gtgcagggtc cgaggttcca t                                                 21

<210> SEQ ID NO 169
<211> LENGTH: 22
<212> TYPE: DNA
<213> ORGANISM: Artificial Sequence
<220> FEATURE:
<223> OTHER INFORMATION: Synthetic (Reverse transcription primer)

<400> SEQUENCE: 169
gtgcagggtc cgaggttcca tc                                                22

<210> SEQ ID NO 170
<211> LENGTH: 23
<212> TYPE: DNA
<213> ORGANISM: Artificial Sequence
<220> FEATURE:
<223> OTHER INFORMATION: Synthetic (Reverse transcription primer)

<400> SEQUENCE: 170
gtgcagggtc cgaggttcca tca                                               23

<210> SEQ ID NO 171
<211> LENGTH: 24
<212> TYPE: DNA
<213> ORGANISM: Artificial Sequence
<220> FEATURE:
<223> OTHER INFORMATION: Synthetic (Reverse transcription primer)

<400> SEQUENCE: 171
gtgcagggtc cgaggttcca tcat                                              24

<210> SEQ ID NO 172
<211> LENGTH: 4
<212> TYPE: DNA
<213> ORGANISM: Artificial Sequence
<220> FEATURE:
<223> OTHER INFORMATION: Synthetic

<400> SEQUENCE: 172 cctc                                                                     4

<210> SEQ ID NO 173
```

```
<211> LENGTH: 8
<212> TYPE: DNA
<213> ORGANISM: Artificial Sequence
<220> FEATURE:
<223> OTHER INFORMATION: Synthetic

<400> SEQUENCE: 173 ccgccctc                                                              8

<210> SEQ ID NO 174
<211> LENGTH: 10
<212> TYPE: DNA
<213> ORGANISM: Artificial Sequence
<220> FEATURE:
<223> OTHER INFORMATION: Synthetic

<400> SEQUENCE: 174
acccgccctc                                                           10

<210> SEQ ID NO 175
<211> LENGTH: 12
<212> TYPE: DNA
<213> ORGANISM: Artificial Sequence
<220> FEATURE:
<223> OTHER INFORMATION: Synthetic

<400> SEQUENCE: 175
ccacccgccc tc                                                        12

<210> SEQ ID NO 176
<211> LENGTH: 14
<212> TYPE: DNA
<213> ORGANISM: Artificial Sequence
<220> FEATURE:
<223> OTHER INFORMATION: Synthetic

<400> SEQUENCE: 176
ctccacccgc cctc                                                      14

<210> SEQ ID NO 177
<211> LENGTH: 4
<212> TYPE: DNA
<213> ORGANISM: Artificial Sequence
<220> FEATURE:
<223> OTHER INFORMATION: Synthetic

<400> SEQUENCE: 177 tgct                                                                  4

<210> SEQ ID NO 178
<211> LENGTH: 8
<212> TYPE: DNA
<213> ORGANISM: Artificial Sequence
<220> FEATURE:
<223> OTHER INFORMATION: Synthetic

<400> SEQUENCE: 178 gtgctgct                                                              8

<210> SEQ ID NO 179
<211> LENGTH: 10
<212> TYPE: DNA
<213> ORGANISM: Artificial Sequence
<220> FEATURE:
<223> OTHER INFORMATION: Synthetic

<400> SEQUENCE: 179
```

```
acgtgctgct                                                    10

<210> SEQ ID NO 180
<211> LENGTH: 12
<212> TYPE: DNA
<213> ORGANISM: Artificial Sequence
<220> FEATURE:
<223> OTHER INFORMATION: Synthetic

<400> SEQUENCE: 180
ttacgtgctg ct                                                 12

<210> SEQ ID NO 181
<211> LENGTH: 14
<212> TYPE: DNA
<213> ORGANISM: Artificial Sequence
<220> FEATURE:
<223> OTHER INFORMATION: Synthetic

<400> SEQUENCE: 181
atttacgtgc tgct                                               14

<210> SEQ ID NO 182
<211> LENGTH: 16
<212> TYPE: DNA
<213> ORGANISM: Artificial Sequence
<220> FEATURE:
<223> OTHER INFORMATION: Synthetic

<400> SEQUENCE: 182
atatttacgt gctgct                                             16
```